US011560349B2

(12) United States Patent
Miyake et al.

(10) Patent No.: US 11,560,349 B2
(45) Date of Patent: Jan. 24, 2023

(54) HALOALKENYL ALKOXYMETHYL ETHER COMPOUND AND A PROCESS FOR PREPARING A TERMINAL CONJUGATED ALKADIEN-1-YL ACETATE COMPOUND AND A TERMINAL CONJUGATED ALKADIEN-1-OL COMPOUND THEREFROM

(71) Applicant: Shin-Etsu Chemical Co., Ltd., Tokyo (JP)

(72) Inventors: Yuki Miyake, Joetsu (JP); Takeshi Kinsho, Niigata (JP); Ryo Komatsu, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 17/489,905

(22) Filed: Sep. 30, 2021

(65) Prior Publication Data
US 2022/0106253 A1 Apr. 7, 2022

(30) Foreign Application Priority Data

Oct. 2, 2020 (JP) .............................. JP2020-167452

(51) Int. Cl.
| | |
|---|---|
| *C07C 67/297* | (2006.01) |
| *C07C 43/313* | (2006.01) |
| *C07C 29/132* | (2006.01) |
| *C07C 29/147* | (2006.01) |
| *C07C 43/15* | (2006.01) |
| *C07C 67/04* | (2006.01) |
| *C07C 67/287* | (2006.01) |

(52) U.S. Cl.
CPC .......... *C07C 67/297* (2013.01); *C07C 29/132* (2013.01); *C07C 29/147* (2013.01); *C07C 43/15* (2013.01); *C07C 43/313* (2013.01); *C07C 67/04* (2013.01); *C07C 67/287* (2013.01)

(58) Field of Classification Search
CPC ..... C07C 67/297; C07C 67/287; C07C 43/15; C07C 43/313; C07C 29/132; C07C 29/147
See application file for complete search history.

(56) References Cited

FOREIGN PATENT DOCUMENTS

| KR | 20180056877 | 5/2018 | |
|---|---|---|---|
| WO | WO 2018/150379 A2 * | 8/2018 | ............. C07C 57/03 |

OTHER PUBLICATIONS

Gardette, M., et al., General methodology for the synthesis of conjugated dienic insect sex pheromones, Tetrahedron, vo. 40, No. 14, pp. 2741-2750 (Year: 1984).*

Ochiai, M., et al., Steroselective synthesis of E- and Z-9,11-Dodecadien-1-yl acetates: The major sex pheromones of the red bollworm moth, Chern. Pharm. Bull., 31(5), pp. 1641-1645 (Year: 1983).*
U.S. Appl. No. 17/489,898, filed Miyake et al., filed Sep. 30, 2021.
U.S. Appl. No. 17/489,908, Miyake et al., filed Sep. 30, 2021.
"Nickel Boride" Encyclopedia of Reagents for Organic Synthesis, vol. 6, pp. 3694-3699 (2001).
Abstracts of the 1st Latin American Meeting of Chemical Ecology, Colonia del Sacramento, Uruguay (200 pages) (Oct. 17-20, 2010).
Mozuraitis et al. "Identification of Minor Sex Pheromone Components of the Poplar Clearwing Moth Paranthrene tabaniformis (Lepidoptera, Sesiidae)" Zeitschrift für Naturforschung C, 62:138-142 (2007).
Naka et al. "Synthesis and Characterization of 3,13-and 2,13-Octadecadienyl Compounds for Identification of the Sex Pheromone Secreted by a Clearwing Moth, Nokona pernix" Bioscience, Biotechnology, and Biochemistry, 70(2):508-516 (2006).
Nielsen et al. "Response of Male Clearwing Moths to Caged Virgin Females, Female Extracts, and Synthetic Sex Attractants" Environmental Entomology, 4(3):451-454 (1975).
Sasaerila et al. "Identification of Sex Pheromone Components of Nettle Caterpillar, Setothosea asigna" Journal of Chemical Ecology, 23(9):2187-2196 (1997).
Sasaerila et al. "Sex Pheromone Components of Nettle Caterpillar, Setora nitens" Journal of Chemical Ecology, 26(8):1983-1990 (2000).
Siderhurst et al. "n-Butyl (E)-7,9-decadienoate: sex pheromone component of the nettle caterpillar, Darna pallivitta" Entomologia Experimentalis et Applicata, 125:63-69 (2007).
Vickers et al. "Sex pheromone components of the clearwing borer, Carmenta chrysophanes (Meyrick) (Lepidoptera: Sesiidae): Provisional identification and field tests" Australian Journal of Entomology, 40:69-73 (2001).
Legrand et al. "Synthesis and Field Tests of Sex Pheromone Components of the Leafroller Argyrotaenia sphaleropa" Z Naturforsch C J Biosci., 59(9-10):708-712 (2004).

(Continued)

Primary Examiner — Yate' K Cutliff
(74) Attorney, Agent, or Firm — Myers Bigel, P.A.

(57) ABSTRACT

The present invention relates to a haloalkenyl alkoxymethyl ether compound of the following general formula (1): $R^1CH_2OCH_2OCH_2CH_2CH=CH(CH_2)_aX^1$ (1) wherein $R^1$ represents a hydrogen atom, an n-alkyl group having 1 to 9 carbon atoms, or a phenyl group, $X^1$ represents a halogen atom, and "a" represents an integer of 3 to 14. The present invention also relates to processes for preparing a terminal conjugated alkadien-1-yl acetate compound of the following general formula (5): $CH_2=CHCH=CH(CH_2)_aOAc$ (5) wherein "a" is as defined above, and Ac represents an acetyl group, and a terminal conjugated alkadien-1-ol compound of the following general formula (6): $CH_2=CHCH=CH(CH_2)_aOH$ (6) wherein "a" is as defined above, from the haloalkenyl alkoxymethyl ether compound (1).

6 Claims, No Drawings

(56) References Cited

OTHER PUBLICATIONS

Wakamura et al. "Sex pheromone of the blue-striped nettle grub moth Parasa lepida (Cramer) (Lepidoptera: Limacodidae): Identification and field attraction" Applied Entomology and Zoology, 42(3):347-352 (2007).
Yadav et al. "Short and Stereoselective Syntheses of Pheromone Components of Aproaerema Modicella" Synthetic Communications, 25(24):4035-4043 (1995).

* cited by examiner

HALOALKENYL ALKOXYMETHYL ETHER COMPOUND AND A PROCESS FOR PREPARING A TERMINAL CONJUGATED ALKADIEN-1-YL ACETATE COMPOUND AND A TERMINAL CONJUGATED ALKADIEN-1-OL COMPOUND THEREFROM

TECHNICAL FIELD

The present invention relates to a haloalkenyl alkoxymethyl ether compound and a process for preparing a terminal conjugated alkadien-1-yl acetate compound and a terminal conjugated alkadien-1-ol compound therefrom.

BACKGROUND ART

There exist many species of lepidopteran pests which use an acetate compound having a terminal conjugated diene skeleton (hereinafter referred to as "terminal conjugated alkadien-1-yl acetate compound") or an alcohol compound having a terminal conjugated diene skeleton (hereinafter referred to as "terminal conjugated alkadien-1-ol compound") as a sex pheromone. For example, one of sex pheromones of South American tortricid moth (*Argyrotaenia sphaleropa*) which is an apple pest in South America, is (11Z)-11,13-tetradecadien-1-yl acetate; one of the sex pheromones of Groundnut leafminer (*Aproaerema modicella*) which is a peanut pest in Southeast Asia, is (7Z)-7,9-decadien-1-yl acetate; and a sex pheromone of *Parasa lepida* is (7Z)-7,9-decadien-1-ol. In recent years, with the increase of environmental awareness, pest control methods have been attracting attention wherein an amount of sprayed pesticide is reduced, and utilization of sex pheromones is expected as one of them (Non-Patent Literatures 1, 2 and 3 listed below).

For example, processes for preparing (11Z)-11,13-tetradecadien-1-yl acetate, sex pheromone of *Awotaenia sphaleropa,* and (11Z)-11,13-tetradecadien-1-ol were reported, as processes for preparing a terminal conjugated alkadien-1-yl acetate compound and a terminal conjugated alkadien-1-ol compound (Non-Patent Literature 2 listed below). Specifically, the hydroxyl group of a starting material, 11-bromoundecan-1-ol, is acetylated with acetic anhydride to synthesize 11-bromoundecan-1-yl acetate. Next, the 11-bromoundecan-1-yl acetate thus obtained was reacted with triphenylphosphine to prepare a phosphonium salt, followed by a reaction with a base, and then, subjected to a Wittig reaction with acrolein at −78° C. to prepare (11Z)-11,13-tetradecadien-1-yl acetate. Subsequently, the (11Z)-11,13-tetradecadien-1-yl acetate thus obtained was subjected to hydrolysis with potassium hydroxide in the presence of methanol to obtain (11Z)-11,13-tetradecadien-1-ol (Non-Patent Literature 1 listed below).

Processes for preparing (7Z)-7,9-decadien-1-yl acetate, sex pheromone of *Aproaerema modicella,* and (7Z)-7,9-decadien-1-ol, sex pheromone of *Parasalepida,* were reported as processes for preparing a terminal conjugated alkadien-1-yl acetate compound and a terminal conjugated alkadien-1-ol compound (Non-Patent Literature 2 listed below). Specifically, a starting material, 2-(chloromethyl) tetrahydrofuran, was reacted with propyl bromide in ammonia in the presence of lithium amide by to open the tetrahydrofuran ring so as to synthesize 4-octyn-1-ol. Next, the 4-octyn-1-ol thus obtained is subjected to an alkyne zipper reaction with 1,3-diaminopropane to synthesize 7-octyn-1-ol, followed by a coupling reaction with vinyl-bromide in the presence of tetrakis(triphenylphosphine) palladium and copper iodide, and a catalytic reduction to synthesize (7Z)-7,9-decadien-1-ol. Subsequently, the hydroxyl group of the (7Z)-7,9-decadien-1-ol thus obtained is acetylated to prepare (7Z)-7,9-decadien-1-yl acetate (Non-Patent Literatures 2 and 3 listed below).

LIST OF THE LITERATURES

Non-Patent Literature

[Non-Patent Literature 1] C. Ricard Unelius et al., 2004, Z. Naturforsch. 59c: 708-712.

[Non-Patent Literature 2] J. S. Yadav et al. , 1995, Synthetic Communications., 25 (24): 4035-4043.

[Non-Patent Literature 3] S. Wakamura et al., 2007, Appl. Entomol. Zool., 42 (3): 347-352.

Problems to be Solved by the Invention

In the Non-Patent Literature 1, acrolein which has a low boiling point, a strong odor and polymerizability is used in the synthetic process, which makes it difficult to utilize the method in industrial preparation. Also, the Wittig reaction is carried out at −78° C. in the synthetic process and, therefore, a special reaction equipment is required, which make the process economically less advantageous. Further, the total yield is as low as less than 15% in the synthesis process.

In the Non-Patent Literature 2, a special raw material, 2-(chloromethyl) tetrahydrofuran having a strong peculiar odor, is used. Ammonia is also used as a solvent. Ammonia has a strong peculiar odor and, therefore, is designated as a malodorous substance by the Malodor Prevention Law. Ammonia is toxic to a human body and, therefore, is designated as a hazardous gas. These require a special equipment for the reaction and post-treatment and makes the process unsuitable for industrial production. In addition, an expensive palladium catalyst is used, which make the process economically less advantageous. Further, hyperhydrogenation of the terminal double bond occurs in the hydrogenation of the enyne compound having a double bond at the terminal, which is not desirable in view of purity.

The present invention has been made in these circumstances, and aims to provide a process for efficiently preparing a terminal conjugated alkadien-1-yl acetate compound and a terminal conjugated alkadien-1-ol compound.

SUMMARY OF THE INVENTION

As a result of the intensive researches to overcome the aforesaid problems of the prior art, the present inventors have found that a haloalkenyl alkoxymethyl ether compound is a useful intermediate for the preparation of a terminal conjugated alkadien-1-yl acetate compound and a terminal conjugated alkadien-1-ol compound. The present inventors have also found that use of the haloalkenyl alkoxymethyl ether compound makes it possible to efficiently prepare the terminal conjugated alkadien-1-yl acetate compound and the terminal conjugated alkadien-1-ol compound, which compounds may have the various number of carbon atoms in shorter steps and in a high purity, and thus have completed the present invention.

According to one aspect of the present invention, there is provided a process for preparing a terminal conjugated alkadien-1-yl acetate compound of the following general formula (5):

$$CH_2=CHCH=CH(CH_2)_aOAc \quad (5)$$

wherein "a" represents an integer of 3 to 14, and Ac represents an acetyl group, the process comprising:

dealkoxymethylating a haloalkenyl alkoxymethyl ether compound of the following general formula (1):

$$R^1CH_2OCH_2OCH_2CH_2CH=CH(CH_2)_aX^1 \quad (1)$$

wherein $R^1$ represents a hydrogen atom, an n-alkyl group having 1 to 9 carbon atoms, or a phenyl group, $X^1$ represents a halogen atom, and "a" is as defined above to prepare a halo-3-alken-1-ol compound of the following general formula (2):

$$HOCH_2CH_2CH=CH(CH_2)_aX^1 \quad (2)$$

wherein $X^1$ and "a" are as defined above;

acetoxylating the halo-3-alken-1-ol compound (2) to prepare a hydroxyalkenyl acetate compound of the following general formula (3):

$$HOCH_2CH_2CH=CH(CH_2)_aOAc \quad (3)$$

wherein "a" and Ac are as defined above;

halogenating the hydroxyalkenyl acetate compound (3) to prepare a haloalkenyl acetate compound of the following general formula (4):

$$X^2CH_2CH_2CH=CH(CH_2)_aOAc \quad (4)$$

wherein $X^2$ represents a halogen atom, and "a" and Ac are as defined above; and subjecting the haloalkenyl acetate compound (4) to an elimination reaction in the presence of a base to prepare the terminal conjugated alkadien-1-yl acetate compound (5).

According to another aspect of the present invention, there is provided a process for preparing a terminal conjugated alkadien-1-ol compound of the following general formula (6):

$$CH_2=CHCH=CH(CH_2)_aOH \quad (6)$$

wherein "a" represents an integer of 3 to 14, the process comprising:

the aforesaid process for preparing the terminal conjugated alkadien-1-yl acetate compound (5), and deacetylating the terminal conjugated alkadien-1-yl acetate compound (5) to prepare the terminal conjugated alkadien-1-ol compound (6).

According to another aspect of the present invention, in the process for preparing the terminal conjugated alkadien-1-ol compound (6), the elimination reaction and the deacetylation are carried out in parallel in the presence of a base.

According to another aspect of the present invention, there is provided a haloalkenyl alkoxymethyl ether compound of the following general formula (1):

$$R'CH_2OCH_2OCH_2CH_2CH=CH(CH_2)_aX^1 \quad (1)$$

wherein $R^1$ represents a hydrogen atom, an n-alkyl group having 1 to 9 carbon atoms, or a phenyl group, $X^1$ represents a halogen atom, and "a" represents an integer of 3 to 14.

According to the present invention, it is possible to prepare the terminal conjugated alkadien-1-yl acetate compound (5) and the terminal conjugated alkadien-1-ol compound (6), which compounds may have the various number of carbon atoms, in shorter steps, in a high yield, and in a high purity.

DETAILED DESCRIPTION OF THE PREFERRED EMBODIMENTS

Haloalkenyl Alkoxymethyl Ether Compound (1)

First, the haloalkenyl alkoxymethyl ether compound of the following general formula (1) will be explained.

$$R^1CH_2OCH_2OCH_2CH_2CH=CH(CH_2)_nX^1 \quad (1)$$

$R^1$ represents a hydrogen atom, an n-alkyl group having 1 to 9 carbon atoms, preferably 1 to 5 carbon atoms, more preferably 1 to 2 carbon atoms, or a phenyl group.

Examples of the n-alkyl group, $R^1$, include linear saturated hydrocarbon groups such as a methyl group, an ethyl group, an n-propyl group, an n-butyl group, an n-pentyl group, an n-hexyl group, an n-heptyl group, an n-octyl group, and an n-nonyl group.

"a" represents an integer of 3 to 14, preferably for preparing a pheromon of lepidopteran pest, 3 to 10, more preferably 6 to 10, even more preferably 6, 7 or 10.

$X^1$ represents a halogen atom such as a fluorine atom, a chlorine atom, a bromine atom, or an iodine atom. A chlorine atom, a bromine atom, or an iodine atom, particularly a chlorine atom and a bromine atom, are preferred in view of the suppression of side reactions in the step of dealkoxymethylation.

Specific examples of the haloalkenyl alkoxymethyl ether compound (1) include the following compounds:

7-halo-3-heptenyl alkoxymethyl ether compounds (a=3) such as 7-chloro-3-heptenyl methoxymethyl ether, 7-chloro-3-heptenyl ethoxymethyl ether, 7-bromo-3-heptenyl methoxymethyl ether, 7-bromo-3-heptenyl ethoxymethyl ether, 7-iodo-3-heptenyl methoxymethyl ether, and 7-iodo-3-heptenyl ethoxymethyl ether;

8-halo-3-octenyl alkoxymethyl ether compounds (a=4) such as 8-chloro-3-octenyl methoxymethyl ether, 8-chloro-3-octenyl ethoxymethyl ether, 8-bromo-3-octenyl methoxymethyl ether, 8-bromo-3-octenyl ethoxymethyl ether, 8-iodo-3-octenyl methoxymethyl ether, and 8-iodo-3-octenyl ethoxymethyl ether;

9-halo-3-noneyl alkoxymethyl ether compounds (a=5) such as 9-chloro-3-noneyl methoxymethyl ether, 9-chloro-3-noneyl ethoxymethyl ether, 9-bromo-3-noneyl methoxymethyl ether, 9-bromo-3-noneyl ethoxymethyl ether, 9-iodo-3-noneyl methoxymethyl ether, and 9-iodo-3-noneyl ethoxymethyl ether;

10-halo-3-decenyl alkoxymethyl ether compounds (a=6) such as 10-chloro-3-decenyl methoxymethyl ether, 10-chloro-3-decenyl ethoxymethyl ether, 10-chloro-3-decenyl propoxymethyl ether, 10-chloro-3-decenyl butoxymethyl ether, 10-chloro-3-decenyl pentyloxymethyl ether, 10-chloro-3-decenyl hexyloxymethyl ether, 10-chloro-3-decenyl heptyloxymethyl ether, 10-chloro-3-decenyl octyloxymethyl ether, 10-chloro-3-decenyl nonyloxymethyl ether, 10-chloro-3-decenyl decyloxymethyl ether, 10-chloro-3-decenyl benzyloxymethyl ether, 10-bromo-3-decenyl methoxymethyl ether, 10-bromo-3-decenyl ethoxymethyl ether, 10-bromo-3-decenyl propoxymethyl ether, 10-bromo-3-decenyl butoxymethyl ether 10-bromo-3-decenyl pentyloxymethyl ether, 10-bromo-3-decenyl hexyloxymethyl ether, 10-bromo-3-decenyl heptyloxymethyl ether, 10-bromo-3-decenyl octyloxymethyl ether, 10-bromo-3-decenyl nonyloxymethyl ether, 10-bromo-3-decenyl decyloxymethyl ether, 10-bromo-3-decenyl benzyloxymethyl ether, 10-iodo-3-decenyl methoxymethyl ether, 10-iodo-3-decenyl ethoxymethyl ether, 10-iodo-3-decenyl propoxymethyl ether, 10-iodo-3-decenyl butoxymethyl ether, 10-iodo-3-decenyl pentyloxymethyl ether, 10-iodo-3- decenyl hexyloxymethyl ether, 10-iodo-3-decenyl heptyloxymethyl ether, 10-iodo-3-decenyl octyloxymethyl ether, 10-iodo-3-decenyl nonyloxymethyl ether, 10-iodo-3-decenyl decyloxymethyl ether, and 10-iodo-3-decenyl benzyloxymethyl ether;

11-halo-3-undecenyl alkoxymethyl ether compounds (a=7) such as 11-chloro-3-undecenyl methoxymethyl ether, 11-chloro-3-undecenyl ethoxymethyl ether, 11-bromo-3-undecenyl methoxymethyl ether, 11-bromo-3-undecenyl ethoxymethyl ether, 11-iodo-3-undecenyl methoxymethyl ether, and 11-iodo-3-undecenyl ethoxymethyl ether;

12-halo-3-dodecenyl alkoxymethyl ether compounds (a=8) such as 12-chloro-3-dodecenyl methoxymethyl ether, 12-chloro-3-dodecenyl ethoxymethyl ether, 12-bromo-3-dodecenyl methoxymethyl ether, 12-bromo-3-dodecenyl ethoxymethyl ether, 12-iodo-3-dodecenyl methoxymethyl ether, and 12-iodo-3-dodecenyl ethoxymethyl ether;

13-halo-3-tridecenyl alkoxymethyl ether compounds (a=9) such as 13-chloro-3-tridecenyl methoxymethyl ether, 13-chloro-3-tridecenyl ethoxymethyl ether, 13-bromo-3-tridecenyl methoxymethyl ether, 13-bromo-3-tridecenyl ethoxymethyl ether, 13-iodo-3-tridecenyl methoxymethyl ether, and 13-iodo-3-tridecenyl ethoxymethyl ether;

14-halo-3-tetradecenyl alkoxymethyl ether compounds (a=10) such as 14-chloro-3-tetradecenyl methoxymethyl ether, 14-chloro-3-tetradecenyl ethoxymethyl ether, 14-chloro-3-tetradecenyl propoxymethyl ether, 14-chloro-3-tetradecenyl butoxymethyl ether, 14-chloro-3-tetradecenyl pentyloxymethyl ether, 14-chloro-3-tetradecenyl hexyloxymethyl ether, 14-chloro-3-tetradecenyl heptyloxymethyl ether, 14-chloro-3-tetradecenyl octyloxymethyl ether, 14-chloro-3-tetradecenyl nonyloxymethyl ether, 14-chloro-3-tetradecenyl decyloxymethyl ether, 14-chloro-3-tetradecenyl benzyloxymethyl ether, 14-bromo-3-tetradecenyl methoxymethyl ether, 14-bromo-3-tetradecenyl ethoxymethyl ether, 14-bromo-3-tetradecenyl propoxymethyl ether, 14-bromo-3-tetradecenyl butoxymethyl ether, 14-bromo-3-tetradecenyl pentyloxymethyl ether, 14-bromo-3-tetradecenyl hexyloxymethyl ether, 14-bromo-3-tetradecenyl heptyloxymethyl ether, 14-bromo-3-tetradecenyl octyloxymethyl ether, 14-bromo-3-tetradecenyl nonyloxymethyl ether, 14-bromo-3-tetradecenyl decyloxymethyl ether, 14-bromo-3-tetradecenyl benzyloxymethyl ether, 14-iodo-3-tetradecenyl methoxymethyl ether, 14-iodo-3-tetradecenyl ethoxymethyl ether, 14-iodo-3-tetradecenyl propoxymethyl ether, 14-iodo-3-tetradecenyl butoxymethyl ether, 14-iodo-3-tetradecenyl pentyloxymethyl ether, 14-iodo-3-tetradecenyl hexyloxymethyl ether, 14-iodo-3-tetradecenyl heptyloxymethyl ether, 14-iodo-3-tetradecenyl octyloxymethyl ether, 14-iodo-3-tetradecenyl nonyloxymethyl ether, 14-iodo-3-tetradecenyl decyloxymethyl ether, and 14-iodo-3-tetradecenyl benzyloxymethyl ether;

15-halo-3-pentadecenyl alkoxymethyl ether compounds (a=11) such as 15-chloro-3-pentadecenyl methoxymethyl ether, 15-chloro-3-pentadecenyl ethoxymethyl ether, 15-bromo-3-pentadecenyl methoxymethyl ether, 15-bromo-3-pentadecenyl ethoxymethyl ether, 15-iodo-3-pentadecenyl methoxymethyl ether, and 15-iodo-3-pentadecenyl ethoxymethyl ether;

16-halo-3-hexadecenyl alkoxymethyl ether compounds (a=12) such as 16-chloro-3-hexadecenyl methoxymethyl ether, 16-chloro-3-hexadecenyl ethoxymethyl ether, 16-bromo-3-hexadecenyl methoxymethyl ether, 16-bromo-3-hexadecenyl ethoxymethyl ether, 16-iodo-3-hexadecenyl methoxymethyl ether, and 16-iodo-3-hexadecenyl ethoxymethyl ether;

17-halo-3-heptadecenyl alkoxymethyl ether compounds (a=13) such as 17-chloro-3-heptadecenyl methoxymethyl ether, 17-chloro-3-heptadecenyl ethoxymethyl ether, 17-bromo-3-heptadecenyl methoxymethyl ether, 17-bromo-3-heptadecenyl ethoxymethyl ether, 17-iodo-3-heptadecenyl methoxymethyl ether, and 17-iodo-3-heptadecenyl ethoxymethyl ether; and 18-halo-3-octadecenyl alkoxymethyl ether compounds (a=14) such as 18-chloro-3-octadecenyl methoxymethyl ether, 18-chloro-3-octadecenyl ethoxymethyl ether, 18-bromo-3-octadecenyl methoxymethyl ether, 18-bromo-3-octadecenyl ethoxymethyl ether, 18-iodo-3-octadecenyl methoxymethyl ether, and 18-iodo-3-octadecenyl ethoxymethyl ether.

Among these haloalkenyl alkoxymethyl ether compounds (1), the 10-halo-3-decenyl alkoxymethyl ether compound (a=6) and the 14-halo-3-tetradecenyl alkoxymethyl ether compound (a=10) are preferred for preparing (7Z)-7,9-decadien-1-yl acetate, sex pheromone of $Aproaerema\ modicella$, and (11Z)-11,13-tetradecadien-1-yl acetate), sex pheromon of $Argyrotaenia\ sphaleropa$. The 11-halo-3-undecenyl alkoxymethyl ether compound (a=7) is preferred as a useful intermediate in preparing (9E)-9,11-dodecadienal, sex pheromon of $Setothosea\ asigna$, and (9Z)-9,11-dodecadienal, a sex pheromone of $Setora\ nitens$.

The haloalkenyl alkoxymethyl ether compound (1) may be synthesized by various synthetic methods shown below, depending on the number "a" in the general formula (1). It should be noted in the following description of the synthesis method that the description on a compound is not limited only to the case where the compound is prepared according to the specific synthesis method shown below, but applies also to a case where the compound is prepared according to a method other than the aforesaid specific synthesis method.

When "a" represents an integer of 5 to 14, the haloalkenyl alkoxymethyl ether compound (1) may be synthesized, for example, according to the following reaction scheme comprising at least 5 steps.

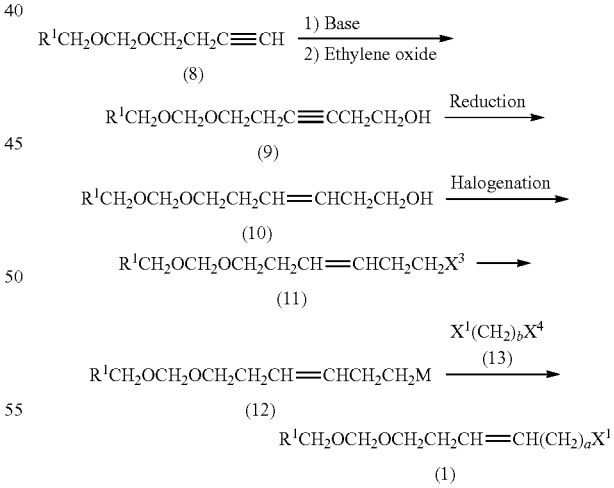

First, an alkoxymethyl 3-butynyl ether compound of the general formula (8) is reacted with a base, and then reacted with ethylene oxide to increase the number of carbon atoms, thereby obtaining a 6-hydroxy-3-hexynyl alkoxymethyl ether compound of the general formula (9) (first step). The carbon-carbon triple bond of the obtained 6-hydroxy-3-hexynyl alkoxymethyl ether compound (9) is reduced to obtain a 6-hydroxy-3-hexenyl alkoxymethyl ether compound of the general formula (10) (second step). The hydroxyl group of the obtained 6-hydroxy-3-hexenyl alkoxymethyl ether compound (10) is halogenated to obtain a 6-halo-3-hexenyl alkoxymethyl ether compound of the general formula (11) (third step). The obtained 6-halo-3-hexenyl alkoxymethyl ether compound (11) is reacted with, for example, magnesium or an organolithium reagent in a solvent to obtain a nucleophilic reagent, 6-(alkoxymethoxy)-3-hexenyl compound of the general formula (12) (fourth step). Then, the obtained nucleophilic reagent, 6-(alkoxymethoxy)-3-hexenyl compound (12), is subjected to a coupling reaction with a dihaloalkane compound of the general formula (13) to obtain the haloalkenyl alkoxymethyl ether compound (1) having the increased number of carbon atoms (fifth step).

The aforesaid process for preparing the haloalkenyl alkoxymethyl ether compound (1) will be explained in more detail below.

The alkoxymethyl 3-butynyl ether compound (8) will be explained below.

$R^1$ in the general formula (8) is as defined for the general formula (1).

Specific examples of the alkoxymethyl 3-butynyl ether compound (8) include methoxymethyl 3-butynyl ether, ethoxymethyl 3-butynyl ether, propoxymethyl 3-butynyl ether, butoxymethyl 3-butynyl ether, pentyloxymethyl 3-butynyl ether, hexyloxymethyl 3-butynyl ether, heptyloxymethyl 3-butynyl ether, octyloxymethyl 3-butynyl ether, nonyloxymethyl3-butynyl ether, decyloxymethyl 3-butynyl ether, and benzyloxymethyl 3-butynyl ether.

Examples of the base used in a homologation reaction include organometallic reagents such as n-butyllithium, tert-butyllithium, methylmagnesium chloride, methylmagnesium bromide, sodium acetylide, and potassium acetylide; and metal hydride reagents such as sodium hydride and potassium hydride. The organometallic reagents are preferred in view of the reactivity.

An amount of the base used is preferably 1.0 to 5.0 mol, more preferably 1.0 to 2.0 mol, per mol of the alkoxymethyl 3-butynyl ether compound (8) in view of the reactivity.

An amount of the ethylene oxide is preferably 1.0 to 10.0 mol, more preferably 1.0 to 3.0 mol, per mol of the alkoxymethyl 3-butynyl ether compound (8) in view of the reactivity.

A solvent may be used in the aforesaid homologation reaction, if necessary.

Examples of the solvent include usual solvents, for example, ethers such as diethyl ether, dibutyl ether, 4-methyltetrahydropyran, tetrahydrofuran (THF), cyclopentylmethylether, and 1,4-dioxane; hydrocarbons such as hexane, heptane, benzene, toluene, xylene, and cumene; chlorinated solvents such as trichloroethylene, dichloromethane, and chloroform; aprotic polar solvents such as dimethyl sulfoxide, γ-butyrolactone (GBL), N-methylpyrrolidone, N,N-dimethylformamide, N,N-dimethylacetamide, and hexamethylphosphoric triamide; and nitriles such as acetonitrile and propionitrile. Ethers such as diethyl ether, tetrahydrofuran, and 4-methyltetrahydropyran are preferred in view of the reactivity.

The solvent may be used alone or in combination thereof, if necessary. The solvent may be commercially available one.

An amount of the solvent is preferably 50 to 3,000 g, more preferably 100 to 1,200 g, per mol of the alkoxymethyl 3-butynyl ether compound (8) in view of the reactivity.

The 6-hydroxy-3-hexynyl alkoxymethyl ether compound (9) will be explained below.

$R^1$ in the general formula (9) is as defined for the general formula (1).

Specific examples of the 6-hydroxy-3-hexynyl alkoxymethyl ether compound (9) include 6-hydroxy-3-hexynyl methoxymethyl ether, 6-hydroxy-3-hexynyl ethoxymethyl ether, 6-hydroxy-3-hexynyl propoxymethyl ether, 6-hydroxy-3-hexynyl butoxymethyl ether, 6-hydroxy-3-hexynyl pentyloxymethyl ether, 6-hydroxy-3-hexynyl hexyloxymethyl ether, 6-hydroxy-3-hexynyl heptyloxymethyl ether, 6-hydroxy-3-hexynyl octyloxymethyl ether, 6-hydroxy-3-hexynyl nonyloxymethyl ether, 6-hydroxy-3-hexynyl decyloxymethyl ether, and 6-hydroxy-3-hexynyl benzyloxymethyl ether.

Examples of the reduction to synthesize the 6-hydroxy-3-hexenyl alkoxymethyl ether compound (10) include (i) a catalytic hydrogenation, (ii) a reduction using a zinc compound in an alcohol solvent, (iii) a hydroboration with a dialkylborane, followed by protonation, (iv) a reduction using potassium hydroxide and N,N-dimethylformamide (DMF) in the presence of a palladium catalyst such as palladium acetate, (v) a hydrosilylation to form vinyl silane, followed by desilylation, (vi) hydroalumination, and (vii) a Birch reduction. Preferred are the catalytic hydrogenation (i), the reduction using a zinc compound (ii), the hydroboration, followed by protonation (iii), and the hydroalumination (vi) in view of the selectivity and productivity. The catalytic hydrogenation (i) is preferred, if it is desired to form a carbon-carbon double bond in the 6-hydroxy-3-hexenyl alkoxymethyl ether compound (10) in a Z-selective manner. The hydroalumination (vi) is preferred, if it is desired to form a carbon-carbon double bond in the 6-hydroxy-3-hexenyl alkoxymethyl ether compound (10) in an E-selective manner.

(i) Catalytic Hydrogenation

The catalytic hydrogenation is carried out by supplying a hydrogen gas in the presence of a metal catalyst.

Examples of the metal catalyst used in the catalytic hydrogenation include Lindlar catalyst; nickel catalysts such as P-2 nickel boride catalyst (Thomas J. Caggiano et al. Encyclopedia of Reagents for Organic Synthesis: 3694-3699) (hereinafter also referred to as "P-2 Ni catalyst"); and palladium catalysts such as palladium carbon and Pd-PEI that is palladium carbon poisoned by polyethylenimine polymer (PEI). Lindlar catalyst and nickel catalysts are preferred in view of the economy.

An amount of the metal catalyst varies, depending on a catalyst to be used, and is preferably 0.01 to 50 g per mol of the 6-hydroxy-3-hexynyl alkoxymethyl ether compound (9) in view of the reactivity, when the catalyst is solid, like Lindlar catalyst. The P-2 Ni catalyst is preferably used in an amount of 0.001 to 0.50 mol, as reduced to a nickel compound, per mol of the 6-hydroxy-3-hexynyl alkoxymethyl ether compound (9).

The solid catalyst may be dispersed in a solvent.

When the metal catalyst is highly active, a catalyst poison may be incorporated, if necessary.

Examples of the catalyst poison include amine compounds such as pyridine, quinoline, and ethylenediamine; phosphorus compounds such as triphenylphosphine, tritolylphosphine, and triethylphosphite; and sulfur compounds such as benzenethiol, diphenyl sulfide, dimethyl sulfide, and dimethyl sulfoxide.

An amount of the catalyst poison varies greatly, depending on a catalyst poison to be used, and is preferably 0.0001 to 10.0 g per mol of the 6-hydroxy-3-hexynyl alkoxymethyl ether compound (9) in view of the reaction rate and geometrical selectivity.

Examples of the solvent used in the catalytic hydrogenation include hydrocarbons such as hexane, heptane, benzene, toluene, xylene, and cumene; nitriles such as acetonitrile and propionitrile; esters such as methyl acetate, ethyl acetate, n-propyl acetate, and n-butyl acetate; and alcohols such as methanol, ethanol, propanol, butanol, pentanol, hexanol, 2-propanol, 2-butanol, and cyclohexanol.

The solvent may be used alone or in combination thereof, if necessary. The solvent may be commercially available one.

When Lindlar catalyst is used, the solvent is preferably a hydrocarbon such as hexane, heptane, toluene, or xylene in view of the reactivity. When a nickel catalyst is used, the solvent is preferably an alcohol such as methanol, ethanol, propanol, butanol, or 2-propanol in view of the reactivity. When a palladium catalyst such as palladium carbon is used, the solvent is preferably an ester such as methyl acetate or ethyl acetate in view of the reactivity.

An amount of the solvent used varies, depending on a catalyst and/or a solvent to be used, and is preferably 0 to 1,000 g per mol of the 6-hydroxy-3-hexynyl alkoxymethyl ether compound (9) in view of the reactivity.

A reaction temperature of the catalytic hydrogenation varies, depending on a catalyst and/or a solvent used, and is preferably 0 to 160° C., more preferably 20 to 100° C., in view of the geometrical selectivity.

A reaction time of the catalytic hydrogenation is preferably 1 to 100 hours in view of the yield.

(ii) Reduction Using a Zinc Compound in an Alcohol Solvent

The reduction is carried out using a zinc compound in an alcohol solvent.

An alcohol used as the solvent has preferably 1 to 10, more preferably 1 to 5, carbon atoms. Examples of the alcohol used as the solvent include linear alcohol compounds such as methanol, ethanol, propanol, butanol, pentanol, hexanol, heptanol, octanol, nonanol, and decanol; branched alcohol compounds such as 2-propanol and 2-butanol; and cyclic alcohol compounds such as cyclohexanol. Alcohol compounds having 1 to 5 carbon atoms, such as methanol, ethanol, propanol, butanol, pentanol, and 2-propanol, are preferred in view of the reactivity.

An amount of the alcohol is preferably 46 to 1,000 g per mol of the 6-hydroxy-3-hexynyl alkoxymethyl ether compound (9) in view of the reactivity.

The zinc compound refers to metallic zinc or activated zinc as explained below.

An amount of the zinc compound is preferably 1.0 to 1,000 mol, more preferably 1.0 to 200 mol, per mol of the 6-hydroxy-3-hexynyl alkoxymethyl ether compound (9) in view of the reactivity.

The reduction may take a longer time due to the low reactivity of zinc. Then, an activator which activates zinc may be added or a zinc compound which has been activated in advance may be used.

Examples of the activator include 1,2-dibromoethane, cuprous chloride, cuprous bromide, cuprous iodide, lithium bromide, iodine, and chlorotrimethylsilane.

The activator may be used alone or in combination thereof, if necessary.

An amount of the activator is preferably 0.01 to 10.0 mol per mol of the 6-hydroxy-3-hexynyl alkoxymethyl ether compound (9) in view of the reactivity.

The activated zinc may be prepared, for example, by treating metallic zinc with an acid such as hydrochloric acid; reducing zinc chloride with metallic lithium in tetrahydrofuran; or reacting metallic zinc with 1,2-dibromoethane and lithium dibromocuprate in tetrahydrofuran.

A reaction temperature of the reduction varies, depending on a solvent to be used, and is preferably 20 to 120° C. in view of the reactivity.

A reaction time of the reduction is preferably 1 to 150 hours in view of the completion of the reaction.

(iii) Hydroboration With a Dialkylborane, Followed by Protonation

For the reduction, hydroboration is first carried out with a dialkylborane in a solvent.

The dialkylborane used in the hydroboration has preferably 4 to 18, more preferably 6 to 12, carbon atoms.

Examples of the dialkylborane include dicyclohexylborane, diisoamylborane, disiamylborane, 9-borabicyclo[3.3.1]nonane (9-BBN), diisopinocampheylborane, catecholborane, and pinacolborane. Dicyclohexylborane and diisoamylborane are preferred in view of the reactivity.

An amount of the dialkylborane is preferably 1.0 to 4.0 mol per mol of the 6-hydroxy-3-hexynyl alkoxymethyl ether compound (9) in view of the reactivity.

Examples of the solvent used in the hydroboration include ethers such as tetrahydrofuran, diethyl ether, dibutyl ether, 4-methyltetrahydropyran, cyclopentylmethylether, 1,4-dioxane, and diethyleneglycol dimethyl ether; and hydrocarbons such as hexane, heptane, benzene, toluene, xylene, and cumene. Ethers such as tetrahydrofuran, 4-methyltetrahydropyran, and diethyleneglycol dimethyl ether are more preferred in view of the reactivity.

The solvent may be used alone or in combination thereof, if necessary. The solvent may be commercially available one.

An amount of the solvent is preferably 100 to 3,000 g per mol of the 6-hydroxy-3-hexynyl alkoxymethyl ether compound (10) in view of the reactivity.

A reaction temperature of the hydroboration is preferably −20 to 50° C. in view of the geometrical selectivity.

A reaction time of the hydroboration varies, depending on a reaction temperature and/or a reaction scale, and is preferably 1 to 100 hours in view of the reactivity.

For the reduction, protonation is carried out with an acid in a solvent after the hydroboration.

Examples of the acid used in the protonation include carboxylic acids such as acetic acid, propionic acid, butyric acid, pentanoic acid, pivalic acid, heptanoic acid, trifluoroacetic acid, chloroacetic acid, formic acid, and oxalic acid; sulfonic acids such as p-toluenesulfonic acid; and mineral acids such as sulfuric acid, hydrochloric acid, nitric acid, and phosphoric acid. Carboxylic acids such as acetic acid and propionic acid are preferred in view of the reactivity.

An amount of the acid is preferably 2.0 to 20.0 mol per mol of the 6-hydroxy-3-hexynyl alkoxymethyl ether compound (9) in view of the reactivity.

The species and an amount of the solvent are the same as those in the hydroboration, because the protonation is carried out subsequently in the hydroboration reaction system.

A reaction temperature of the protonation varies, depending on a reagent to be used, and is preferably 0 to 150° C. in view of the reaction rate.

A reaction time of the protonation varies, depending on a reaction temperature and/or a reaction scale, and is preferably 1 to 70 hours in view of the reactivity.

(iv) Reduction Using Potassium Hydroxide and N,N-dimethylformamide (DMF) in the Presence of a Palladium Catalyst Such as Palladium Acetate The reduction is carried out using potassium hydroxide and N,N-dimethylformamide (DMF) in the presence of a palladium catalyst such as palladium acetate, preferably at 100 to 180° C. for 6 to 100 hours.

(v) Hydrosilylation to Form Vinylsilane, Followed by Desilylation

The hydrosilylation is carried out using a metal catalyst, such as Wilkinson catalyst or Trost catalyst, and a trialkylsilane.

An amount of the metal catalyst is preferably 0.0001 to 4.0 mol, more preferably 0.001 to 1.0 mol, per mol of the 6-hydroxy-3-hexynyl alkoxymethyl ether compound (9) in view of the reactivity.

The hydrosilylation is preferably carried out at 5 to 100° C. for 1 to 100 hours.

The desilylation after the hydrosilylation is preferably carried out using, for example, at least one out of acid such as sulfuric acid or hydrochloric acid, hydrogen iodide, acetyl chloride, titanium tetrachloride, and iodine at 5 to 80° C. for 1 to 100 hours.

(vi) Hydroalumination

The hydroalumination is carried out using lithium aluminum hydride.

An amount of lithium aluminum hydride is preferably 0.25 to 4.0 mol, more preferably 0.35 to 2.0 mol, per mol of the 6-hydroxy-3-hexynyl alkoxymethyl ether compound (9) in view of the reactivity.

Examples of the solvent used in the hydroalumination include ethers such as diethyl ether, dibutyl ether, 4-methyltetrahydropyran, tetrahydrofuran (THF), cyclopentylmethylether, 1,4-dioxane, and diethyleneglycol dimethyl ether; and hydrocarbons such as hexane, heptane, benzene, toluene, xylene, and cumene. Ethers such as tetrahydrofuran, 4-methyltetrahydropyran, and diethyleneglycol dimethyl ether are preferred in view of the reactivity.

The solvent may be used alone or in combination thereof, if necessary. The solvent may be commercially available one.

The hydroalumination is preferably carried out at 20 to 180° C. for 1 to 100 hours.

(vii) Birch Reduction

The Birch reduction is carried out using a metal in an amine or alcohol.

Examples of the metal include alkaline metals such as potassium, sodium, and lithium; and alkaline earth metals such as calcium and magnesium.

Examples of the amine include ammonia; and lower amines such as methylamine, ethylamine, and propylamine.

Example of the alcohol include methanol, ethanol, and 2-methylpropanol.

The Birch reduction is preferably carried out at −78 to 20° C. for 1 to 100 hours.

The geometry of the carbon-carbon double bond of the 6-hydroxy-3-hexenyl alkoxymethyl ether compound (10) may be constructed selectively in an E- or Z-configuration by choosing reduction conditions.

The 6-hydroxy-3-hexenyl alkoxymethyl ether compound (10) will be explained below.

$R^1$ in the general formula (10) is as defined for the general formula (1).

Specific examples of the 6-hydroxy-3-hexenyl alkoxymethyl ether compound (10) include 6-hydroxy-3-hexenyl methoxymethyl ether, 6-hydroxy-3-hexenyl ethoxymethyl ether, 6-hydroxy-3-hexenyl propoxymethyl ether, 6-hydroxy-3-hexenyl butoxymethyl ether, 6-hydroxy-3-hexenyl pentyloxymethyl ether, 6-hydroxy-3-hexenyl hexyloxymethyl ether, 6-hydroxy-3-hexenyl heptyloxymethyl ether, 6-hydroxy-3-hexenyl octyloxymethyl ether, 6-hydroxy-3-hexenyl nonyloxymethyl ether, 6-hydroxy-3-hexenyl decyloxymethyl ether, and 6-hydroxy-3-hexenyl benzyloxymethyl ether.

The halogenation reaction for synthesizing the 6-halo-3-hexenyl alkoxymethyl ether compound (11) may be carried out, for example, by tosylating the hydroxyl group with a p-toluenesulfonyl halide compound, followed by halogenation with a lithium halide compound, or by directly halogenating the hydroxyl group with a halogenating agent.

Examples of the halogenating agent include halogen molecules such as chlorine, bromine, and iodine; hydrogen halide compounds such as hydrogen chloride, hydrogen bromide, and hydrogen iodide; methanesulfonyl halide compounds such as methanesulfonyl chloride, methanesulfonyl bromide, and methanesulfonyl iodide; benzenesulfonyl halide compounds such as benzenesulfonyl chloride, benzenesulfonyl bromide, and benzenesulfonyl iodide; p-toluenesulfonyl halide compounds such as p-toluenesulfonyl chloride, p-toluenesulfonyl bromide, and p-toluenesulfonyl iodide; phosphorus halide compounds such as phosphorous trichloride, phosphorous pentachloride, and phosphorus tribromide; carbon tetrahalide compounds such as carbon tetrachloride, carbon tetrabromide, and carbon tetraiodide; alkylsilyl halide compounds such as tetramethylsilyl chloride, tetramethylsilyl bromide, tetramethylsilyl iodide, triethylsilyl chloride, triethylsilyl bromide, triethylsilyl iodide, triisopropylsilyl chloride, triisopropylsilyl bromide, triisopropylsilyl iodide, tert-butyldimethylsilyl chloride, tert-butyldimethylsilyl bromide, and tert-butyldimethylsilyl iodide; oxalyl halide compounds such as oxalyl chloride, oxalyl bromide, and oxalyl iodide; and N-halosuccinimide compounds such as N-chlorosuccinimide, N-bromosuccinimide, and N-iodosuccinimide. A methanesulfonyl halide compound, a benzenesulfonyl halide compound, and a p-toluenesulfonyl halide compound, particularly a methanesulfonyl halide compound, are preferred in view of the suppression of side reactions.

The halogenating agent may be used alone or in combination thereof, if necessary. The halogenating agent may be commercially available one.

An amount of the halogenating agent used is preferably 0.8 to 5.0 mol, more preferably 1.0 to 2.5 mol, per mol of the 6-hydroxy-3-hexenyl alkoxymethyl ether compound (10).

A base may be incorporated in the halogenation reaction, if necessary.

Examples of the base include hydroxides such as sodium hydroxide, potassium hydroxide, calcium hydroxide, and magnesium hydroxide; carbonates such as sodium carbonate, potassium carbonate, calcium carbonate, and magnesium carbonate; amines such as triethylamine, N,N-diisopropylethylamine, piperidine, pyrrolidine, pyridine, lutidine, 4-dimethylaminopyridine, N,N-dimethylaniline, N,N-diethylaniline, and 1,8-diazabicydo[5.4.0]-7-undecene (DBU); and phosphines such as tributylphosphine, triphenylphosphine, and tritolylphosphine.

When the halogenating agent is a methanesulfonyl halide compound, a benzenesulfonyl halide compound, or a p-toluenesulfonyl halide compound, the base is preferably an amine, more preferably pyridines such as pyridine, lutidine, or 4-dimethylaminopyridine.

The base may be used alone or in combination thereof, if necessary. The base may be commercially available one.

An amount of the base is preferably 0 to 8.0 mol, more preferably 0 to 3.0 mol, per mol of the 6-hydroxy-3-hexenyl alkoxymethyl ether compound (10) in view of the yield and/or economy.

A metal salt may be incorporated in the halogenation reaction, if necessary.

Examples of the metal salt include lithium salts such as lithium chloride, lithium bromide, and lithium iodide; sodium salts such as sodium chloride, sodium bromide, and sodium iodide; potassium salts such as potassium chloride, potassium bromide, and potassium iodide; calcium salts such as calcium chloride, calcium bromide, and calcium iodide; and magnesium salts such as magnesium chloride, magnesium bromide, and magnesium iodide.

The metal salt may be used alone or in combination thereof, if necessary. The metal salt may be commercially available one.

An amount of the metal salt is preferably 0 to 30.0 mol, more preferably 0 to 5.0 mol, per mol of the 6-hydroxy-3-hexenyl alkoxymethyl ether compound (10) in view of the reactivity.

Although the metal salt increases a concentration of halide ions in the reaction system to thereby enhance the reactivity, it is preferred in view of the economy and/or environmental protection not to incorporate the metal salt.

A solvent may be incorporated in the halogenation reaction, if necessary.

Examples of the solvent include usual solvents, for example, ethers such as diethyl ether, dibutyl ether, 4-methyltetrahydropyran, tetrahydrofuran (THF), cyclopentylmethylether, and 1,4-dioxane; hydrocarbons such as hexane, heptane, benzene, toluene, xylene, and cumene; chlorinated solvents such as trichloroethylene, dichloromethane, and chloroform; aprotic polar solvents such as dimethyl sulfoxide, γ-butyrolactone (GBL), N-methylpyrrolidone (NMP), N,N-dimethylformamide (DMF), N,N-dimethylacetamide (DMAC), and hexamethylphosphoric triamide (HMPA); nitriles such as acetonitrile and propionitrile; and esters such as methyl acetate, ethyl acetate, n-propyl acetate, and n-butyl acetate. 4-Methyltetrahydropyran, dichloromethane, chloroform, γ-butyrolactone, N-methylpyrrolidone, N,N-dimethylformamide, N,N-dimethylacetamide, and acetonitrile are preferred in view of the reactivity. γ-Butyrolactone and acetonitrile are particularly preferred in view of the safety.

The solvent may be used alone or in combination thereof, if necessary. The solvent may be commercially available one.

An amount of the solvent used in the halogenation reaction is preferably 0 to 3,000 g, more preferably 0 to 800 g, per mol of the 6-hydroxy-3-hexenyl alkoxymethyl ether compound (10).

The solvent may occupy a part of a reactor space to reduce a space for the starting materials, resulting in a decreased productivity. Therefore, the reaction may be carried out without a solvent or with the base as the solvent.

A reaction temperature of the halogenation varies, depending on a halogenating agent to be used, and is preferably 5 to 180° C. in view of the reactivity.

A reaction time of the halogenation reaction varies, depending on a halogenating agent and/or a reaction scale, and is preferably 0.5 to 100 hours in view of the reactivity.

The 6-halo-3-hexenyl alkoxymethyl ether compound (11) will be explained below.

$R^1$ in the general formula (11) is as defined for the general formula (1).

Specific examples of the 6-halo-3-hexenyl alkoxymethyl ether compound (11) include 6-halo-3-hexenyl methoxymethyl ether, 6-halo-3-hexenyl ethoxymethyl ether, 6-halo-3-hexenyl propoxymethyl ether, 6-halo-3-hexenyl butoxymethyl ether, 6-halo-3-hexenyl pentyloxymethyl ether, 6-halo-3-hexenyl hexyloxymethyl ether, 6-halo-3-hexenyl heptyloxymethyl ether, 6-halo-3-hexenyl octyloxymethyl ether, 6-halo-3-hexenyl nonyloxymethyl ether, 6-halo-3-hexenyl decyloxymethyl ether, and 6-halo-3-hexenyl benzyloxymethyl ether.

The 6-halo-3-hexenyl alkoxymethyl ether compound (11) is converted into a nucleophilic reagent, 6-(alkoxymethoxy)-3-hexenyl compound (12), which is then subjected to a coupling reaction with the dihaloalkane compound (13) to obtain the haloalkenyl alkoxymethyl ether compound (1) having the increased number of carbon atoms.

One example of the process for synthesizing the nucleophilic reagent, 6-(alkoxymethoxy)-3-hexenyl compound (12), comprises reacting the 6-halo-3-hexenyl alkoxymethyl ether compound (11) with magnesium in a solvent to obtain a 6-(alkoxymethoxy)-3-hexenylmagnesium halide compound (12: M=MgZ) which is a Grignard reagent, as shown in the following chemical reaction formula. This process is hereinafter referred to as "conversion with magnesium".

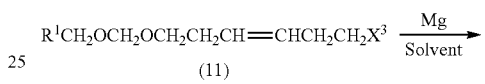

(11)

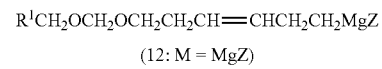

(12: M = MgZ)

An amount of magnesium used in the conversion with magnesium is preferably 1.0 to 2.0 gram atoms per mol of the 6-halo-3-hexenyl alkoxymethyl ether compound (11) in view of the completion of the reaction.

Examples of the solvent used in the conversion with magnesium include ethers such as tetrahydrofuran, diethyl ether, and 4-methyltetrahydropyran; and hydrocarbons such as toluene, xylene, and hexane. Ethers such as tetrahydrofuran, diethyl ether, and 4-methyltetrahydropyran, particularly tetrahydrofuran, is preferred in view of a reaction rate of the Grignard reagent formation.

The solvent may be used alone or in combination thereof, if necessary. The solvent may be commercially available one.

An amount of the solvent used is preferably 50 to 5,000 g, more preferably 100 g to 3,000 g, per mol of the 6-halo-3-hexenyl alkoxymethyl ether compound (11) in view of the reactivity.

A reaction temperature of the conversion with magnesium varies, depending on a solvent to be used, and is preferably 0 to 120° C. in view of the reactivity.

A reaction time of the conversion with magnesium varies, depending on a solvent and/or a reaction scale to be used, and is preferably 0.5 to 100 hours in view of the reactivity.

Another example of the process for synthesizing the nucleophilic reagent, 6-(alkoxymethoxy)-3-hexenyl compound (12), comprises reacting the 6-halo-3-hexenyl alkoxymethyl ether compound (11) with an organolithium reagent in a solvent to obtain a 6-(alkoxymethoxy)-3-hexenyllithium compound (12: M=Li), as shown in the following chemical reaction formula. This process is hereinafter referred to as "conversion with an organolithium reagent")

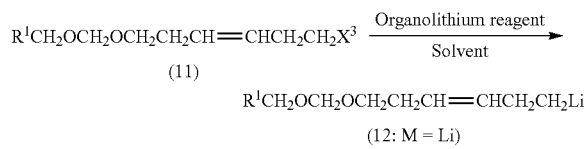

(11)

(12: M = Li)

Examples of the organolithium reagent include linear organolithium reagents such as methyllithium, ethyllithium, n-propyllithium, n-butyllithium, and n-pentyllithium; and branched organolithium reagents such as sec-butyllithium and tert-butyllithium. Methyllithium, n-butyllithium, sec-butyllithium, and tert-butyllithium are preferred in view of the availability.

An amount of the organolithium reagent used is preferably 1.0 to 4.0 mol, more preferably 1.0 to 2.0 mol, per mol of the 6-halo-3-hexenyl alkoxymethyl ether compound (11) in view of the reactivity.

Examples of the solvent used in the conversion with an organolithium reagent include ethers such as tetrahydrofuran, diethyl ether, and 4-methyltetrahydropyran; and hydrocarbons such as toluene, xylene, and hexane. A preferable solvent varies, depending on an organolithium reagent to be used. Generally, tetrahydrofuran, diethyl ether, toluene, and hexane are preferred in view of the reactivity.

The solvent may be used alone or in combination thereof, if necessary. The solvent may be commercially available one.

An amount of the solvent used is preferably 50 to 5,000 g, more preferably 100 to 3,000 g, per mol of the 6-halo-3-hexenyl alkoxymethyl ether compound (11) in view of the reactivity.

A reaction temperature of the conversion with an organolithium reagent varies, depending on a solvent to be used, and is preferably -78 to 25° C. in view of the reactivity.

A reaction time of the conversion with an organolithium reagent varies, depending on a solvent and/or a reaction scale to be used, and is preferably 0.5 to 100 hours in view of the reactivity.

The nucleophilic reagent, 6-(alkoxymethoxy)-3-hexenyl compound (12), will be explained below.

$R^1$ in the general formula (12) is as defined for the general formula (1).

M represents Li or MgZ, wherein Z represents a halogen atom or a 6-(alkoxymethoxy)-3-hexenyl group. Examples of the halogen atom, Z, include a chlorine atom, a bromine atom, and an iodine atom.

Examples of the nucleophilic reagent, 6-(alkoxymethoxy)-3-hexenyl compound (12), include (3E)-6-(alkoxymethoxy)-3-hexenyl compound of the following general formula (12-E), (3Z)-6-(alkoxymethoxy)-3-hexenyl compound of the following general formula (12-Z), and a mixture thereof.

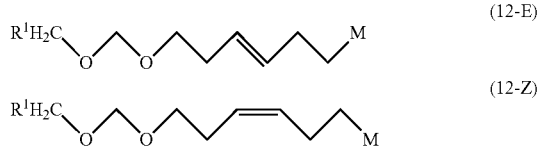

(12-E)

(12-Z)

Specific examples of the nucleophilic reagent, (3E)-6-(alkoxymethoxy)-3-hexenyl compound (12-E), include the following compounds:

(3E)-6-(alkoxymethoxy)-3-hexenyllithium compounds such as (3E)-6-(methoxymethoxy)-3-hexenyllithium, (3E)-6-(ethoxymethoxy)-3-hexenyllithium, (3E)-6-(propoxymethoxy)-3-hexenyllithium, (3E)-6-(butoxymethoxy)-3-hexenyllithium, (3E)-6-(pentyloxymethoxy)-3-hexenyllithium, (3E)-6-(hexyloxymethoxy)-3-hexenyllithium, (3E)-6-(heptyloxymethoxy)-3-hexenyllithium, (3E)-6-(octyloxymethoxy)-3-hexenyllithium, (3E)-6-(nonyloxymethoxy)-3-hexenyllithium, and (3E)-6-(decyloxymethoxy)-3-hexenyllithium;

(3E)-6-(alkoxymethoxy)-3-hexenylmagnesium chloride compounds such as (3E)-6-(methoxymethoxy)-3-hexenylmagnesium chloride, (3E)-6-(ethoxymethoxy)-3-hexenylmagnesium chloride, (3E)-6-(propoxymethoxy)-3-hexenylmagnesium chloride, (3E)-6-(butoxymethoxy)-3-hexenylmagnesium chloride, (3E)-6-(pentyloxymethoxy)-3-hexenylmagnesium chloride, (3E)-6-(hexyloxymethoxy)-3-hexenylmagnesium chloride, (3E)-6-(heptyloxymethoxy)-3-hexenylmagnesium chloride, (3E)-6-(octyloxymethoxy)-3-hexenylmagnesium chloride, (3E)-6-(nonyloxymethoxy)-3-hexenylmagnesium chloride, and (3E)-6-(decyloxymethoxy)-3-hexenylmagnesium chloride;

(3E)-6-(alkoxymethoxy)-3-hexenylmagnesium bromide compounds such as (3E)-6-(methoxymethoxy)-3-hexenylmagnesium bromide, (3E)-6-(ethoxymethoxy)-3-hexenylmagnesium bromide, (3E)-6-(propoxymethoxy)-3-hexenylmagnesium bromide, (3E)-6-(butoxymethoxy)-3-hexenylmagnesium bromide, (3E)-6-(pentyloxymethoxy)-3-hexenylmagnesium bromide, (3E)-6-(hexyloxymethoxy)-3-hexenylmagnesium bromide, (3E)-6-(heptyloxymethoxy)-3-hexenylmagnesium bromide, (3E)-6-(octyloxymethoxy)-3-hexenylmagnesium bromide, (3E)-6-(nonyloxymethoxy)-3-hexenylmagnesium bromide, and (3E)-6-(decyloxymethoxy)-3-hexenylmagnesium bromide; and (3E)-6-(alkoxymethoxy)-3-hexenylmagnesium iodide compounds such as (3E)-6-(methoxymethoxy)-3-hexenylmagnesium iodide, (3E)-6-(ethoxymethoxy)-3-hexenylmagnesium iodide, (3E)-6-(propoxymethoxy)-3-hexenylmagnesium iodide, (3E)-6-(butoxymethoxy)-3-hexenylmagnesium iodide, (3E)-6-(pentyloxymethoxy)-3-hexenylmagnesium iodide, (3E)-6-(hexyloxymethoxy)-3-hexenylmagnesium iodide, (3E)-6-(heptyloxymethoxy)-3-hexenylmagnesium iodide, (3E)-6-(octyloxymethoxy)-3-hexenylmagnesium iodide, (3E)-6-(nonyloxymethoxy)-3-hexenylmagnesium iodide, and (3E)-6-(decyloxymethoxy)-3-hexenylmagnesium iodide.

Among these, (3E)-6-(alkoxymethoxy)-3-hexenylmagnesium halide compounds such as (3E)-6-(alkoxymethoxy)-3-hexenylmagnesium chloride compounds are preferred in view of the availability.

Specific examples of the nucleophilic reagent, (3Z)-6-(alkoxymethoxy)-3-hexenyl compound (12-Z), include the following compounds:

(3Z)-6-(alkoxymethoxy)-3-hexenyllithium compounds such as (3Z)-6-(methoxymethoxy)-3-hexenyllithium, (3Z)-6-(ethoxymethoxy)-3-hexenyllithium, (3Z)-6-(propoxymethoxy)-3-hexenyllithium, (3Z)-6-(butoxymethoxy)-3-hexenyllithium, (3Z)-6-(pentyloxymethoxy)-3-hexenyllithium, (3Z)-6-(hexyloxymethoxy)-3-hexenyllithium, (3Z)-6-(heptyloxymethoxy)-3-hexenyllithium, (3Z)-6-(octyloxymethoxy)-3-hexenyllithium, (3Z)-6-(nonyloxymethoxy)-3-hexenyllithium, and (3Z)-6-(decyloxymethoxy)-3-hexenyllithium;

(3Z)-6-(alkoxymethoxy)-3-hexenylmagnesium chloride compounds such as (3Z)-6-(methoxymethoxy)-3-hexenylmagnesium chloride, (3Z)-6-(ethoxymethoxy)-3-hexenylmagnesium chloride, (3Z)-6-(propoxymethoxy)-3-hexenylmagnesium chloride, (3Z)-6-(butoxymethoxy)-3-hexenylmagnesium chloride, (3Z)-6-(pentyloxymethoxy)-3-hexenylmagnesium chloride, (3Z)-6-(hexyloxymethoxy)-3-hexenylmagnesium chloride, (3Z)-6-(heptyloxymethoxy)-3-hexenylmagnesium chloride, (3Z)-6-(octyloxymethoxy)-3-hexenylmagnesium chloride, (3Z)-6-(nonyloxymethoxy)-3-hexenylmagnesium chloride, and (3Z)-6-(decyloxymethoxy)-3-hexenylmagnesium chloride;

(3Z)-6-(alkoxymethoxy)-3-hexenylmagnesium bromide compounds such as (3Z)-6-(methoxymethoxy)-3-hexenylmagnesium bromide, (3Z)-6-(ethoxymethoxy)-3-hexenylmagnesium bromide, (3Z)-6-(propoxymethoxy)-3-hexenylmagnesium bromide, (3Z)-6-(butoxymethoxy)-3-hexenylmagnesium bromide, (3Z)-6-(pentyloxymethoxy)-3-hexenylmagnesium bromide, (3Z)-6-(hexyloxymethoxy)-3-hexenylmagnesium bromide, (3Z)-6-(heptyloxymethoxy)-3-hexenylmagnesium bromide, (3Z)-6-(octyloxymethoxy)-3-hexenylmagnesium bromide, (3Z)-6-(nonyloxymethoxy)-3-hexenylmagnesium bromide, and (3Z)-6-(decyloxymethoxy)-3-hexenylmagnesium bromide; and (3Z)-6-(alkoxymethoxy)-3-hexenylmagnesium iodide compounds such as (3Z)-6-(methoxymethoxy)-3-hexenylmagnesium iodide, (3Z)-6-(ethoxymethoxy)-3-hexenylmagnesium iodide, (3Z)-6-(propoxymethoxy)-3-hexenylmagnesium iodide, (3Z)-6-(butoxymethoxy)-3-hexenylmagnesium iodide, (3Z)-6-(pentyloxymethoxy)-3-hexenylmagnesium iodide, (3Z)-6-(hexyloxymethoxy)-3-hexenylmagnesium iodide, (3Z)-6-(heptyloxymethoxy)-3-hexenylmagnesium iodide, (3Z)-6-(octyloxymethoxy)-3-hexenylmagnesium iodide, (3Z)-6-(nonyloxymethoxy)-3-hexenylmagnesium iodide, and (3Z)-6-(decyloxymethoxy)-3-hexenylmagnesium iodide.

Among these, (3Z)-6-(alkoxymethoxy)-3-hexenylmagnesium halide compounds such as (3Z)-6-(alkoxymethoxy)-3-hexenylmagnesium chloride compounds are preferred in view of the availability.

The nucleophilic reagent, 6-(alkoxymethoxy)-3-hexenyl compound (12), may be used alone or in combination thereof, if necessary.

The nucleophilic reagent, 6-(alkoxymethoxy)-3-hexenyl compound (12), may be commercially available one or may be prepared in house.

An amount of the nucleophilic reagent, 6-(alkoxymethoxy)-3-hexenyl compound (12), used in the coupling reaction is preferably 0.8 to 3.0 mol, more preferably 1.0 to 1.8 mol, per mol of the 6-halo-3-hexenyl alkoxymethyl ether compound (11) in view of the economy.

The dihaloalkane compound (13) will be explained below.

$R^1$ in the general formula (13) is as defined for the general formula (1), and $X^1$ and $X^4$ represent, independently of each other, a halogen atom such as a fluorine atom, a chlorine atom, a bromine atom, or an iodine atom.

"b" in the general formula (13) represents an integer of 3 to 12, preferably 4 to 8.

The haloalkenyl alkoxymethyl ether compound (1) having a desired number of carbon atoms may be-prepared by choosing the number of carbon number, i.e., "b", of the dihaloalkane compound (13).

An amount of the dihaloalkane compound (13) is preferably 0.7 to 5.0 mol, more preferably 0.7 to 2.5 mol, per mol of the 6-halo-3-hexenyl alkoxymethyl ether compound (11) in view of the reactivity.

Specific examples of the dihaloalkane compound (13) include the following compounds:

1,3-dihalopropane compounds (b=3) such as 1,3-dichloropropane, 1,3-dibromopropane, 1,3-diiodopropane, 1-bromo-3-chloropropane, 1-chloro-3-iodopropane, and 1-bromo-3-iodopropane;

1,4-dihalobutane compounds (b=4) such as 1,4-dichlorobutane, 1,4-dibromobutane, 1,4-diiodobutane, 1-bromo-4-chlorobutane, 1-chloro-4-iodobutane, and 1-bromo-4-iodobutane;

1,5-dihalopentane compounds (b=5) such as 1,5-dichloropentane, 1,5-dibromopentane, 1,5-diiodopentane, 1-bromo-5-chloropentane, 1-chloro-5-iodopentane, and 1-bromo-5-iodopentane;

1,6-dihalohexane compounds (b=6) such as 1,6-dichlorohexane, 1,6-dibromohexane, 1,6-diiodohexane, 1-bromo-6-chlorohexane, 1-chloro-6-iodohexane, and 1-bromo-6-iodohexane;

1,7-dihaloheptane compounds (b=7) such as 1,7-dichloroheptane, 1,7-dibromoheptane, 1,7-diiodoheptane, 1-bromo-7-chloroheptane, 1-chloro-7-iodoheptane, and 1-bromo-7-iodoheptane;

1,8-dihalooctane compounds (b=8) such as 1,8-dichlorooctane, 1,8-dibromooctane, 1,8-diiodooctane, 1-bromo-8-chlorooctane, 1-chloro-8-iodooctane, and 1-bromo-8-iodooctane;

1,9-dihalononane compounds (b=9) such as 1,9-dichlorononane, 1,9-dibromononane, 1,9-diiodononane, 1-bromo-9-chlorononane, 1-chloro-9-iodononane, and 1-bromo-9-iodononane;

1,10-dihalodecane compounds (b=10) such as 1,10-dichlorodecane, 1,10-dibromodecane, 1,10-diiododecane, 1-bromo-10-chlorodecane, 1-chloro-10-iododecane, and 1-bromo-10-iododecane;

1,11-dihaloundecane compounds (b=11) such as 1,11-dichloroundecane, 1,11-dibromoundecane, 1,11-diiodoundecane, 1-bromo-11-chloroundecane, 1-chloro-11-iodoundecane, and 1-bromo-11-iodoundecane; and 1,12-dihalododecane compounds (b=12) such as 1,12-dichlorododecane, 1,12-dibromododecane, 1,12-diiodododecane, 1-bromo-12-chlorododecane, 1-chloro-12-iodododecane, and 1-bromo-12-iodododecane.

The dihaloalkane compound (13) may be used alone or in combination thereof, if necessary. The dihaloalkane compound (13) may be commercially available one or may be prepared in house.

A solvent may be incorporated in the coupling reaction, if necessary. Examples of the solvent include usual solvents, for example, ethers such as diethyl ether, dibutyl ether, 4-methyltetrahydropyran, tetrahydrofuran (THF), cyclopentylmethylether, and 1,4-dioxane; hydrocarbons such as hexane, heptane, benzene, toluene, xylene, and cumene; chlorinated solvents such as trichloroethylene, dichloromethane, and chloroform; aprotic polar solvents such as dimethyl sulfoxide, γ-butyrolactone (GBL), N-methylpyrrolidone (NMP), N,N-dimethylformamide (DMF), N,N-dimethylacetamide (DMAC), and hexamethylphosphoric triamide (HMPA); and nitriles such as acetonitrile and propionitrile. Toluene, tetrahydrofuran, 4-methyltetrahydropyran, and acetonitrile, particularly tetrahydrofuran, are preferred in view of the reactivity.

The solvent may be used alone or in combination thereof, if necessary. The solvent may be commercially available one.

An amount of the solvent used is preferably 30 to 5,000 g, more preferably 50 to 3,000 g, per mol of the 6-halo-3-hexenyl alkoxymethyl ether compound (11) in view of the reactivity.

A catalyst may be incorporated in the coupling reaction, if necessary. Examples of the catalyst include copper compounds including cuprous halides such as cuprous chloride, cuprous bromide, and cuprous iodide, and cupric halides such as cupric chloride, cupric bromide, and cupric iodide; iron compounds such as iron(II) chloride, iron(III) chloride, iron(II) bromide, iron(III) bromide, iron(II) iodide, iron(III) iodide, and iron(III) acetylacetonate; silver compounds such as silver chloride, silver nitrate, and silver acetate; titanium compounds such as titanium tetrachloride, titanium tetrabromide, titanium(IV) methoxide, titanium(IV) ethoxide, titanium(IV) isopropoxide, and titanium (IV) oxide; palladium(II) compounds such as dichlorobis(triphenylphosphine)palladium and dichloro[1,1'-bis(diphenylphosphino)ferrocene]palladium; and nickel compounds such as nickel chloride, dichloro[1,2-bis(diphenylphosphino)ethane]nickel (II), and dichlorobis(triphenylphosphine)nickel(II). When the nucleophilic reagent, 6-(alkoxymethoxy)-3-hexenyl compound (12), is a Grignard reagent, that is, a 6-(alkoxymethoxy)-3-hexenylmagnesium halide compound (12: M=MgZ), copper compounds, particularly cuprous halides such as cuprous chloride, cuprous bromide, and cuprous iodide, are preferred in view of the reactivity and/or economy.

The catalyst may be used alone or in combination thereof, if necessary. The catalyst may be commercially available one.

An amount of the catalyst used is preferably 0.0003 to 0.300 mol, more preferably 0.003 to 0.100 mol, per mol of the 6-halo-3-hexenyl alkoxymethyl ether compound (11) in view of the reaction rate and easy post-processing.

When a catalyst is used in the coupling reaction, a co-catalyst may also be incorporated, if necessary. Examples of the co-catalyst include a trialkyl phosphite compound having 3 to 9 carbon atoms, such as triethyl phosphite; and an arylphosphine compound having 18 to 44 carbon atoms, such as triphenylphosphine, tritolylphosphine, or 2,2'-bis (diphenylphosphino)-1,1'-binaphthyl (BINAP). A trialkyl phosphite, particularly triethyl phosphite, is preferred in view of the reactivity.

The co-catalyst may be used alone or in combination thereof, if necessary. The co-catalyst may be commercially available one.

An amount of the co-catalyst used is preferably 0.0001 to 1.00 mol, more preferably 0.001 to 0.300 mol, per mol of the 6-halo-3-hexenyl alkoxymethyl ether compound (11).

When an organolithium reagent is used in the coupling reaction, N,N,N',N'-tetramethylethylenediamine (TMEDA), hexamethylphosphoric triamide (HMPA), or N,N'-dimethylpropylene urea (DMPU) may be incorporated to improve a reaction rate, if necessary.

When a catalyst is used in the coupling reaction, a lithium halide may also be incorporated, if necessary. Examples of the lithium halide include lithium chloride, lithium bromide, and lithium iodide. Lithium chloride is preferred in view of the reactivity.

An amount of the lithium halide used in the coupling reaction is preferably 0.0001 to 1.00 mol, more preferably 0.001 to 0.300 mol, per mol of the 6-halo-3-hexenyl alkoxymethyl ether compound (11), in view of the reactivity.

A reaction temperature of the coupling reaction varies, depending on the nucleophilic reagent, 6-(alkoxymethoxy)-3-hexenyl compound (12), and is preferably −78 to 80° C., more preferably −25 to 40° C. in view of the reactivity.

A reaction time of the coupling reaction varies, depending on a solvent and/or a reaction scale, and is preferably 0.5 to 100 hours in view of the reactivity.

When "a" represents an integer of 3 to 14, especially 3 to 4, the haloalkenyl alkoxymethyl ether compound (1) may also be synthesized, for example, according to a chemical reaction formula including at least the following two steps.

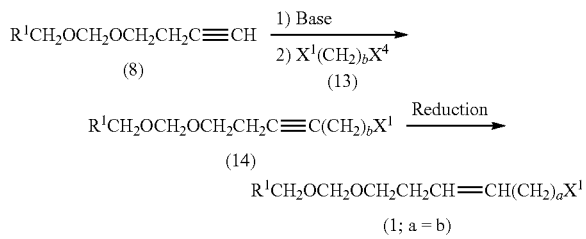

First, an alkoxymethyl 3-butynl ether compound of the general formula (8) is deprotonated in the presence of a base, and then reacted with the dihaloalkane compound (13) to increase the number of caron atoms, resulting in a halo-3-alkynyl alkoxymethyl ether compound of the general formula (14). The carbon-carbon triple bond of the obtained halo-3-alkynyl alkoxymethyl ether compound (14) is reduced to obtain the haloalkenyl alkoxymethyl ether compound (1). le in the general formula (14) is as defined for the general formula (1).

Preparation of the halo-3-alken-1-ol compound (2)

The halo-3-alken-1-ol compound (2) may be prepared by dealkoxymethylating the haloalkenyl alkoxymethyl ether (1), as shown in the following chemical reaction formula.

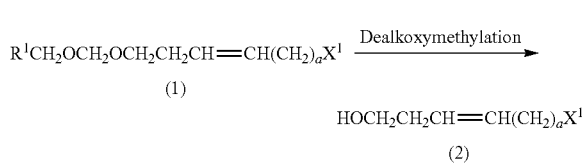

In the dealkoxymethylation, the haloalkenyl alkoxymethyl ether compound (1) may be used alone or in combination thereof, if necessary.

For example, a mixture of a (3E)-10-halo-3-decenyl methoxymethyl ether compound (1: $R^1$=H; a=6) and a (3Z)-10-halo-3-decenyl methoxymethyl ether compound (1: $R^1$=H; a=6)) makes it possible to obtain a mixture of the (3E)-10-halo-3-decen-1-ol compound (2: a=6) and the (3Z)-10-halo-3-decen-1-ol compound (2: a=6).

For example, a mixture of a (3E)-11-halo-3-undecenyl methoxymethyl ether compound (1: $R^1$=H; a=7) and a (3Z)-11-halo-3-undecenyl methoxymethyl ether compound (1: $R^1$=H; a=7) gives a mixture of a (3E)-11-halo-3-undecen-1-ol compound (2: a=7) and a (3Z)-11-halo-3-undecen-1-ol compound (2: a=7).

Further, for example, a mixture of a (3E)-14-halo-3-tetradecenyl methoxymethyl ether compound (1: $R^1$=H; a=10) and a (3Z)-14-halo-3-tetradecenyl methoxymethyl ether compound (1: $R^1$=H; a=10) gives a mixture of a (3E)-14-halo-3-tetradecen-1-ol compound (2: a=10) and a (3Z)-14-halo-3-tetradecen-1-ol compound (2: a=10).

Optimal conditions of the dealkoxymethylation varies, depending on $R^1$. For example, when $R^1$ is a phenyl group, the dealkoxymethylation may be carried out in Birch reduction conditions in which sodium is used in liquid ammonia. When $R^1$ is a hydrogen atom or an n-alkyl group such as a methyl group, the dealkoxymethylation may be carried out using an acid or an alcohol compound (7) mentioned below.

Examples of the acid include inorganic acids such as hydrochloric acid and hydrobromic acid; sulfonic acids such as p-toluenesulfonic acid and benzenesulfonic acid; organic acids such as trifluoroacetic acid, acetic acid, formic acid, and oxalic acid; and Lewis acids such as iodotrimethylsilane and titanium tetrachloride. p-Toluenesulfonic acid, benzenesulfonic acid, hydrochloric acid, and hydrobromic acid, particularly hydrochloric acid and hydrobromic acid, are preferred in view of the suppression of side reactions.

The acid preferably contains a halogen atom corresponding to $X^1$ in the substrate, haloalkenyl alkoxymethyl ether compound (1). For example, when a chloroalkenyl alkoxymethyl ether compound is used as a substrate, hydrochloric acid is preferably chosen. When a bromoalkenyl alkoxymethyl ether compound is used as a substrate, hydrobromic acid is preferably chosen.

The acid may be used alone or in combination thereof, if necessary. The acid may be commercially available one.

An amount of the acid used is preferably 0.0001 to 10.0 mol, more preferably 0.001 to 1.0 mol, per mol of the haloalkenyl alkoxymethyl ether compound (1).

The alcohol compound (7) is represented by the following general formula (7):

$$R^2OH \quad (7)$$

$R^2$ represents a monovalent hydrocarbon group having 1 to 15 carbon atoms, preferably 1 to 6 carbon atoms, in view of the price or availability. Examples of the monovalent hydrocarbon group include linear saturated hydrocarbon groups such as a methyl group, an ethyl group, an n-propyl group, an n-butyl group, an n-pentyl group, an n-hexyl group, an n-heptyl group, an n-octyl group, an n-nonyl group, an n-decyl group, an n-undecyl group, and an n-dodecyl group; branched saturated hydrocarbon groups such as an isopropyl group, a 2-isobutyl group, and a 2-methylbutyl group; linear unsaturated hydrocarbon groups such as a 2-propenyl group; branched unsaturated hydrocarbon groups such as a 2-methyl-2-propenyl group; cyclic saturated hydrocarbon groups such as a cyclopropyl group; and isomers thereof. A part of the hydrogen atoms of the hydrocarbon group may be substituted with a methyl group, an ethyl group, or a hydroxyl group.

The monovalent hydrocarbon group is preferably a methyl group, an ethyl group, an n-propyl group, or an n-butyl group in view of the handling.

Examples of the alcohol compound (7) include linear alcohols such as methanol, ethanol, n-propanol, n-butanol, n-pentanol, n-hexanol, n-heptanol, n-octanol, n-nonanol, n-decanol, n-undecanol, n-dodecanol, n-tridecanol, n-tetradecanol, and n-pentadecanol; branched alcohols such as isopropanol and 2-butanol; and diols such as ethyleneglycol, propyleneglycol, 2-methyl-1,3-propanediol, 2,2-dimethyl-1,3-propanediol, 1,2-dimethyl-1,3-propanediol, 1,3-dimethyl-1,3-propanediol, and 2-methyl-1,4-butanediol. Methanol and ethanol, particularly methanol, are preferred in view of the reactivity.

The alcohol compound (7) may be used alone or in combination thereof, if necessary.

The alcohol compound (7) may be commercially available one.

An amount of the alcohol compound (7) used is preferably 1 to 1,000 mol, more preferably 1 to 100 mol, per mol of the haloalkenyl alkoxymethyl ether compound (1) in view of the reactivity.

A solvent other than the alcohol compound (7) may be used in the dealkoxymethylation, if necessary.

Examples of the solvent include usual solvents, for example, ethers such as diethyl ether, dibutyl ether, 4-methyltetrahydropyran, tetrahydrofuran (THF), cyclopentylmethylether, and 1,4-dioxane; hydrocarbons such as hexane, heptane, benzene, toluene, xylene, and cumene; chlorinated solvents such as trichloroethylene, dichloromethane, and chloroform; aprotic polar solvents such as dimethyl sulfoxide, γ-butyrolactone (GBL), N-methylpyrrolidone (NMP), N,N-dimethylformamide (DMF), N,N-dimethylacetamide (DMAC), and hexamethylphosphoric triamide (HMPA); nitriles such as acetonitrile and propionitrile; and esters such as methyl acetate, ethyl acetate, n-propyl acetate, and n-butyl acetate.

The solvent may be used alone or in combination thereof, if necessary. The solvent may be commercially available one.

An amount of the solvent used in the dealkoxymethylation is preferably 0 to 2,000 g, more preferably 0 to 500 g, per mol of the haloalkenyl alkoxymethyl ether compound (1).

The solvent occupies a space of a reactor to reduce a space for starting material, resulting in a decreased productivity. Therefore, the dealkoxymethylation may be carried out without a solvent.

A reaction temperature of the dealkoxymethylation varies, depending on a haloalkenyl alkoxymethyl ether compound (1) to be used, and is preferably 5 to 180° C. in view of the reactivity.

A reaction time of the dealkoxymethylation varies, depending on a haloalkenyl alkoxymethyl ether compound (1) and/or a reaction scale, and is preferably 1 to 100 hours in view of the reactivity.

In the dealkoxymethylation, a by-produced alkoxymethoxymethane may be distilled off from the reaction system, if necessary, whereby the equilibrium is shifted to the product side to reduce the reaction time.

The halo-3-alken-1-ol compound (2) will be explained below.

$X^1$ and "a" in the general formula (2) are as defined for the general formula (1).

Specific examples of the halo-3-alken-1-ol compound (2) include the following compounds:

7-halo-3-hepten-1-ol compounds (a=3) such as (3Z)-7-chloro-3-hepten-1-ol, (3Z)-7-bromo-3-hepten-1-ol, (3Z)-7-iodo-3-hepten-1-ol, (3E)-7-chloro-3-hepten-1-ol, (3E)-7-bromo-3-hepten-1-ol, and (3E)-7-iodo-3-hepten-1-ol;

8-halo-3-octen-1-ol compounds (a=4) such as (3Z)-8-chloro-3-octen-1-ol, (3Z)-8-bromo-3-octen-1-ol, (3Z)-8-iodo-3-octen-1-ol, (3E)-8-chloro-3-octen-1-ol, (3E)-8-bromo-3-octen-1-ol, and (3E)-8-iodo-3-octen-1-ol;

9-halo-3-nonen-1-ol compounds (a=5) such as (3Z)-9-chloro-3-nonen-1-ol, (3Z)-9-bromo-3-nonen-1-ol, (3Z)-9-iodo-3-nonen-1-ol, (3E)-9-chloro-3-nonen-1-ol, (3E)-9-bromo-3-nonen-1-ol, and (3E)-9-iodo-3-nonen-1-ol;

10-halo-3-decen-1-ol compounds (a=6) such as (3Z)-10-chloro-3-decen-1-ol, (3Z)-10-bromo-3-decen-1-ol, (3Z)-10-iodo-3-decen-1-ol, (3E)-10-chloro-3-decen-1-ol, (3E)-10-bromo-3-decen-1-ol, and (3E)-10-iodo-3-decen-1-ol;

11-halo-3-undecen-1-ol compounds (a=7) such as (3Z)-11-chloro-3-undecen-1-ol, (3Z)-11-bromo-3-undecen-1-ol, (3Z)-11-iodo-3-undecen-1-ol, (3E)-11-chloro-3-undecen-1-ol, (3E)-11-bromo-3-undecen-1-ol, and (3E)-11-iodo-3-undecen-1-ol;

12-halo-3-dodecen-1-ol compounds (a=8) such as (3Z)-12-chloro-3-dodecen-1-ol, (3Z)-12-bromo-3-dodecen-1-ol, (3Z)-12-iodo-3-dodecen-1-ol, (3E)-12-chloro-3-dodecen-1-ol, (3E)-12-bromo-3-dodecen-1-ol, and (3E)-12-iodo-3-dodecen-1-ol;

13-halo-3-tridecen-1-ol compounds (a=9) such as (3Z)-13-chloro-3-tridecen-1-ol, (3Z)-13-bromo-3-tridecen-1-ol, (3Z)-13-iodo-3-tridecen-1-ol, (3E)-13-chloro-3-tridecen-1-ol, (3E)-13-bromo-3-tridecen-1-ol, and (3E)-13-iodo-3-tridecen-1-ol;

14-halo-3-tetradecen-1-ol compounds (a=10) such as (3Z)-14-chloro-3-tetradecen-1-ol, (3Z)-14-bromo-3-tetradecen-1-ol, (3Z)-14-iodo-3-tetradecen-1-ol, (3E)-14-chloro-3-tetradecen-1-ol, (3E)-14-bromo-3-tetradecen-1-ol, and (3E)-14-iodo-3-tetradecen-1-ol;

15-halo-3-pentadecen-1-ol compounds (a=11) such as (3Z)-15-chloro-3-pentadecen-1-ol, (3Z)-15-bromo-3-pentadecen-1-ol, (3Z)-15-iodo-3-pentadecen-1-ol, (3E)-15-chloro-3-pentadecen-1-ol, (3E)-15-bromo-3-pentadecen-1-ol, and (3E)-15-iodo-3-pentadecen-1-ol;

16-halo-3-hexadecen-1-ol compounds (a=12) such as (3Z)-16-chloro-3-hexadecen-1-ol, (3Z)-16-bromo-3-hexadecen-1-ol, (3Z)-16-iodo-3-hexadecen-1-ol, (3E)-16-chloro-3-hexadecen-1-ol, (3E)-16-bromo-3-hexadecen-1-ol, and (3E)-16-iodo-3-hexadecen-1-ol;

17-halo-3-heptadecen-1-ol compounds (a=13) such as (3Z)-17-chloro-3-heptadecen-1-ol, (3Z)-17-bromo-3-heptadecen-1-ol, (3Z)-17-iodo-3-heptadecen-1-ol, (3E)-17-chloro-3-heptadecen-1-ol, (3E)-17-bromo-3-heptadecen-1-ol, and (3E)-17-iodo-3-heptadecen-1-ol; and 18-halo-3-octadecen-1-ol compounds (a=14) such as (3Z)-18-chloro-3-octadecen-1-ol, (3Z)-18-bromo-3-octadecen-1-ol, (3Z)-18-iodo-3-octadecen-1-ol, (3E)-18-chloro-3-octadecen-1-ol, (3E)-18-bromo-3-octadecen-1-ol, and (3E)-18-iodo-3-octadecen-1-ol.

Preparation of the Hydroxyalkenyl Acetate Compound (3)

The hydroxyalkenyl acetate compound (3) may be prepared by acetoxylating the halo-3-alken-1-ol compound (2), as shown in the following chemical reaction formula.

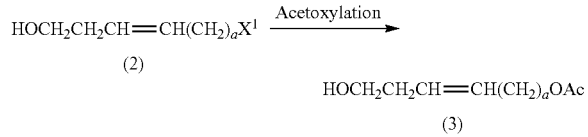

In the acetoxylation, the halo-3-alken-1-ol compound (2) may be used alone or in combination thereof, if necessary.

For example, a mixture of the (3Z)-10-halo-3-decen-1-ol compound (2: a=6) and the (3E)-10-halo-3-decen-1-ol compound (2: a=6) gives a mixture of the (7Z)-10-hydroxy-7-decenyl acetate compound (3: a=6) and the (7E)-10-hydroxy-7-decenyl acetate compound (3: a=6).

For example, a mixture of the (3Z)-11-halo-3-undecen-1-ol compound (2: a=7) and the (3E)-11-halo-3-undecen-1-ol compound (2: a=7) gives a mixture of the (8Z)-11-hydroxy-8-undecenyl acetate compound (3: a=7) and the (8E)-11-hydroxy-8-undecenyl acetate compound (3: a=7).

Further, for example, a mixture of the (3Z)-14-halo-3-tetradecen-1-ol compound (2: a=10) and the (3E)-14-halo-3-tetradecen-1-ol compound (2: a=10) gives a mixture of the (11Z)-14-hydroxy-11-tetradecenyl acetate compound (3: a=10) and the (11E)-14-hydroxy-11-tetradecenyl acetate compound (3: a=10).

The acetoxylation may be carried out using an acetoxylating agent.

Examples of the acetoxylating agent include, for example, alkali metal acetates such as lithium acetate, sodium acetate, and potassium acetate; and alkaline earth metal acetates such as calcium acetate and magnesium acetate. Alkali metal acetates such as sodium acetate and potassium acetate are preferred in view of the reactivity.

An amount of the acetoxylating agent is preferably 1.0 to 10.0 mol, more preferably 1.0 to 3.0 mol, per mol of the halo-3-alken-1-ol compound (2) in view of the reactivity.

The halide may be incorporated in the acetoxylating reaction, if necessary.

Examples of the halide include iodides such as sodium iodide and potassium iodide; and bromides such as sodium bromide and potassium bromide. Iodides such as sodium iodide and potassium iodide are preferred in view of the reactivity.

The halide may be used alone or in combination thereof, if necessary. The halide may be commercially available one.

An amount of the halide used is preferably 0.001 to 10.0 mol, more preferably 0.01 to 3.0 mol, per mol of the halo-3-alken-1-ol compound (2).

A solvent may be incorporated in the acetoxylating reaction, if necessary.

Examples of the solvent include usual solvents, for example, ethers such as tetrahydrofuran, diethyl ether, dibutyl ether, 4-methyltetrahydropyran, cyclopentylmethylether, and 1,4-dioxane; hydrocarbons such as hexane, heptane, benzene, toluene, xylene, and cumene; and polar solvents such as N,N-dimethylformamide, N,N-dimethylacetamide, N-methylpyrrolidone, dimethyl sulfoxide, γ-butyrolactone, acetonitrile, dichloromethane, and chloroform. Preferred are ethers such as tetrahydrofuran and 4-methyltetrahydropyran; and polar solvents such as acetonitrile, N,N-dimethylformamide, N,N-dimethylacetamide, and γ-butyrolactone, and more preferred are acetonitrile, N,N-dimethylformamide, N,N-dimethylacetamide, and γ-butyrolactone, in view of the reactivity.

The solvent may be used alone or in combination thereof, if necessary. The solvent may be commercially available one.

An amount of the solvent is preferably 50 to 5,000 g, more preferably 200 to 2,000 mol, per mol of the halo-3-alken-1-ol compound (2) in view of the reactivity.

The hydroxyalkenyl acetate compound (3) will be explained below.

In the general formula (3), Ac represents an acetyl group and "a" is as defined for the general formula (1).

Specific examples of the hydroxyalkenyl acetate compound (3) include the following compounds:

7-hydroxy-4-heptenyl acetate compounds (a=3) such as (4Z)-7-hydroxy-4-heptenyl acetate and (4E)-7-hydroxy-4-heptenyl acetate;

8-hydroxy-5-octenyl acetate compounds (a=4) such as (5Z)-8-hydroxy-5-octenyl acetate and (5E)-8-hydroxy-5-octenyl acetate;

9-hydroxy-6-nonenyl acetate compounds (a=5) such as (6Z)-9-hydroxy-6-nonenyl acetate and (6E)-9-hydroxy-6-nonenyl acetate;

10-hydroxy-7-decenyl acetate compounds (a=6) such as (7Z)-10-hydroxy-7-decenyl acetate and (7E)-10-hydroxy-7-decenyl acetate;

11-hydroxy-8-undecenylic acid acetate compounds (a=7) such as (8Z)-11-hydroxy-8-undecenyl acetate and (8E)-11-hydroxy-8-undecenyl acetate;

12-hydroxy-9-dodecenyl acetate compounds (a=8) such as (9Z)-12-hydroxy-9-dodecenyl acetate and (9E)-12-hydroxy-9-dodecenyl acetate;

13-hydroxy-10-tridecenyl acetate compounds (a=9) such as (10Z)-13-hydroxy-10-tridecenyl acetate and (10E)-13-hydroxy-10-tridecenyl acetate;

14-hydroxy-11-tetradecenyl acetate compounds (a=10) such as (11Z)-14-hydroxy-11-tetradecenyl acetate and (11E)-14-hydroxy-11-tetradecenyl acetate;

15-hydroxy-12-pentadecenyl acetate compounds (a=11) such as (12Z)-15-hydroxy-12-pentadecenyl acetate and (12E)-15-hydroxy-12-pentadecenyl acetate;

16-hydroxy-13-hexadecenyl acetate compounds (a=12) such as (13Z)-16-hydroxy-13-hexadecenyl acetate and (13E)-16-hydroxy-13-hexadecenyl acetate;

17-hydroxy-14-heptadecenyl acetate compounds (a=13) such as (14Z)-17-hydroxy-14-heptadecenyl acetate and (14E)-17-hydroxy-14-heptadecenyl acetate; and 18-hydroxy-15-octadecenyl acetate compounds (a=14) such as (15Z)-18-hydroxy-15-octadecenyl acetate and (15E)-18-hydroxy-15-octadecenyl acetate.

Preparation of the Haloalkenyl Acetate Compound (4)

The haloalkenyl acetate compound (4) may be prepared by halogenating the hydroxyalkenyl acetate compound (3), as shown in the following chemical reaction formula.

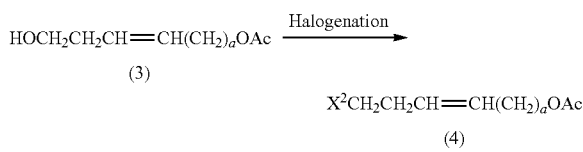

The hydroxyalkenyl acetate compound (3) may be used alone or in combination thereof, if necessary.

For example, a mixture of the (7Z)-10-hydroxy-7-decenyl acetate compound (3: a=6) and the (7E)-10-hydroxy-7-decenyl acetate compound (3: a=6) gives a mixture of the (7Z)-10-halo-7-decenyl acetate compound (4: a=6) and the (7E)-10-halo-7-decenyl acetate compound (4: a=6).

For example, a mixture of the (8Z)-11-hydroxy-8-undecenyl acetate compound (3: a=7) and the (8E)-11-hydroxy-8-undecenyl acetate compound (3: a=7) gives a mixture of the (8Z)-11-halo-8-undecenyl acetate compound (4: a=7) and the (8E)-11-halo-8-undecenyl acetate compound (4: a=7).

Further, for example, a mixture of the (11Z)-14-hydroxy-11-tetradecenyl acetate compound (3: a=10) and the (11E)-14-hydroxy-11-tetradecenyl acetate compound (3: a=10) gives a mixture of the (11Z)-14-halo-11-tetradecenyl acetate compound (4: a=10) and the (11E)-14-halo-11-tetradecenyl acetate compound (4: a=10).

The halogenation reaction may be carried out, for example, by tosylating the hydroxyl group with a p-toluenesulfonyl halide compound, followed by halogenation with a lithium halide compound, or by directly halogenating the hydroxyl group with a halogenating agent.

Examples of the halogenating agent include halogen molecules such as chlorine, bromine, and iodine; hydrogen halide compounds such as hydrogen chloride, hydrogen bromide, and hydrogen iodide; methanesulfonyl halide compounds such as methanesulfonyl chloride, methanesulfonyl bromide, and methanesulfonyl iodide; benzenesulfonyl halide compounds such as benzenesulfonyl chloride, benzenesulfonyl bromide, and benzenesulfonyl iodide; p-toluenesulfonyl halide compounds such as p-toluenesulfonyl chloride, p-toluenesulfonyl bromide, and p-toluenesulfonyl iodide; phosphorus halide compounds such as phosphorous trichloride, phosphorous pentachloride, and phosphorus tribromide; carbon tetrahalide compounds such as carbon tetrachloride, carbon tetrabromide, and carbon tetraiodide; alkylsilyl halide compounds such as tetramethylsilyl chloride, tetramethylsilyl bromide, tetramethylsilyl iodide, triethylsilyl chloride, triethylsilyl bromide, triethylsilyl iodide, triisopropylsilyl chloride, triisopropylsilyl bromide, triisopropylsilyl iodide, tert-butyldimethylsilyl chloride, tert-butyldimethylsilyl bromide, and tert-butyldimethylsilyl iodide; oxalyl halide compounds such as oxalyl chloride, oxalyl bromide, and oxalyl iodide; and N-halosuccinimide compounds such as N-chlorosuccinimide, N-bromosuccinimide, and N-iodosuccinimide. A methanesulfonyl halide compound, a benzenesulfonyl halide compound, and a p-toluenesulfonyl halide compound, particularly a methanesulfonyl halide compound, are preferred in view of the suppression of side reactions.

The halogenating agent may be used alone or in combination thereof, if necessary. The halogenating agent may be commercially available one.

An amount of the halogenating agent used is preferably 0.8 to 5.0 mol, more preferably 1.0 to 2.5 mol, per mol of the hydroxyalkenyl acetate compound (3).

A base may be incorporated in the halogenation reaction, if necessary.

Examples of the base include hydroxides such as sodium hydroxide, potassium hydroxide, calcium hydroxide, and magnesium hydroxide; carbonates such as sodium carbonate, potassium carbonate, calcium carbonate, and magnesium carbonate; and amines such as triethylamine, N,N-diisopropylethylamine, piperidine, pyrrolidine, pyridine, lutidine, 4-dimethylaminopyridine, N,N-dimethylaniline, N,N-diethylaniline, and 1,8-diazabicyclo[5.4.0]-7-undecene (DBU).

When the halogenating agent is a methanesulfonyl halide compound, a benzenesulfonyl halide compound, or a p-toluenesulfonyl halide compound, the base is preferably an amine, more preferably pyridines such as pyridine, lutidine, or 4-dimethylaminopyridine.

The base may be used alone or in combination thereof, if necessary. The base may be commercially available one.

An amount of the base is preferably 0 to 8.0 mol, more preferably 0 to 3.0 mol, per mol of the hydroxyalkenyl acetate compound (3) in view of the yield and/or economy.

A metal salt may be incorporated in the halogenation reaction, if necessary.

Examples of the metal salt include lithium salts such as lithium chloride, lithium bromide, and lithium iodide; sodium salts such as sodium chloride, sodium bromide, and sodium iodide; potassium salts such as potassium chloride, potassium bromide, and potassium iodide; calcium salts such as calcium chloride, calcium bromide, and calcium iodide; and magnesium salts such as magnesium chloride, magnesium bromide, and magnesium iodide.

The metal salt may be used alone or in combination thereof, if necessary. The metal salt may be commercially available one.

An amount of the metal salt is preferably 0 to 30.0 mol, more preferably 0 to 5.0 mol, per mol of the hydroxyalkenyl acetate compound (3) in view of the reactivity.

Although the metal salt increases a concentration of halide ions in a reaction system to thereby enhance the reactivity, it is preferred not to incorporate the metal salt in view of the economy and/or environmental protection.

A solvent may be incorporated in the halogenation reaction, if necessary.

Examples of the solvent include usual solvents, for example, ethers such as diethyl ether, dibutyl ether, 4-methyltetrahydropyran, tetrahydrofuran (THF), cyclopentylmethylether, and 1,4-dioxane; hydrocarbons such as hexane, heptane, benzene, toluene, xylene, and cumene; chlorinated solvents such as trichloroethylene, dichloromethane, and chloroform; aprotic polar solvents such as dimethyl sulfoxide, γ-butyrolactone (GBL), N-methylpyrrolidone (NMP), N,N-dimethylformamide (DMF), N,N-dimethylacetamide (DMAC), and hexamethylphosphoric triamide (HMPA); nitriles such as acetonitrile and propionitrile; and esters such as methyl acetate, ethyl acetate, n-propyl acetate, and n-butyl acetate. 4-Methyltetrahydropyran, dichloromethane, chloroform, γ-butyrolactone, N-methylpyrrolidone, N,N-dimethylformamide, N,N-dimethylacetamide, and acetonitrile are preferred in view of the reactivity. γ-Butyrolactone and acetonitrile are particularly preferred in view of safety.

The solvent may be used alone or in combination thereof, if necessary. The solvent may be commercially available one.

An amount of the solvent used in the halogenation reaction is preferably 0 to 3,000 g, more preferably 0 to 800 g, per mol of the hydroxyalkenyl acetate compound (3).

The solvent may occupy a part of a reactor space to reduce a space for the starting materials, resulting in a decreased productivity. Therefore, the reaction may be carried out without a solvent or with the base as the solvent.

A reaction temperature of the halogenation varies, depending on a halogenating agent to be used, and is preferably 5 to 180° C. in view of the reactivity.

A reaction time of the halogenation reaction varies, depending on a halogenating agent and/or a reaction scale, and is preferably 1 to 100 hours in view of the reactivity.

The haloalkenyl acetate compound (4) will be explained below.

$X^2$ in the general formula (4) represents a halogen atom such as a fluorine atom, a chlorine atom, a bromine atom, or an iodine atom. "a" is as defined for the general formula (1), and Ac is as defined for the general formula (3).

Specific examples of the haloalkenyl acetate compound (4) include the following compounds:

7-halo-4-heptenyl acetate compounds (a=3) such as (4Z)-7-chloro-4-heptenyl acetate, (4Z)-7-bromo-4-heptenyl acetate, (4Z)-7-iodo-4-heptenyl acetate, (4E)-7-chloro-4-heptenyl acetate, (4E)-7-bromo-4-heptenyl acetate, and (4E)-7-iodo-4-heptenyl acetate;

8-halo-5-octenyl acetate compounds (a=4) such as (5Z)-8-chloro-5-octenyl acetate, (5Z)-8-bromo-5-octenyl acetate, (5Z)-8-iodo-5-octenyl acetate, (5E)-8-chloro-5-octenyl acetate, (5E)-8-bromo-5-octenyl acetate, and (5E)-8-iodo-5-octenyl acetate;

9-halo-6-nonenyl acetate compounds (a=5) such as (6Z)-9-chloro-6-nonenyl acetate, (6Z)-9-bromo-6-nonenyl acetate, (6Z)-9-iodo-6-nonenyl acetate, (6E)-9-chloro-6-nonenyl acetate, (6E)-9-bromo-6-nonenyl acetate, and (6E)-9-iodo-6-nonenyl acetate;

10-halo-7-decenyl acetate compounds (a=6) such as (7Z)-10-chloro-7-decenyl acetate, (7Z)-10-bromo-7-decenyl acetate, (7Z)-10-iodo-7-decenyl acetate, (7E)-10-chloro-7-decenyl acetate, (7E)-10-bromo-7-decenyl acetate, and (7E)-10-iodo-7-decenyl acetate;

11-halo-8-undecenyl acetate compounds (a=7) such as (8Z)-11-chloro-8-undecenyl acetate, (8Z)-11-bromo-8-undecenyl acetate, (8Z)-11-iodo-8-undecenyl acetate, (8E)-11-chloro-8-undecenyl acetate, (8E)-11-bromo-8-undecenyl acetate, and (8E)-11-iodo-8-undecenyl acetate;

12-halo-9-dodecenyl acetate compounds (a=8) such as (9Z)-12-chloro-9-dodecenyl acetate, (9Z)-12-bromo-9-dodecenyl acetate, (9Z)-12-iodo-9-dodecenyl acetate, (9E)-12-chloro-9-dodecenyl acetate, (9E)-12-bromo-9-dodecenyl acetate, and (9E)-12-iodo-9-dodecenyl acetate;

13-halo-10-tridecenyl acetate compounds (a=9) such as (10Z)-13-chloro-10-tridecenyl acetate, (10Z)-13-bromo-10-tridecenyl acetate, (10Z)-13-iodo-10-tridecenyl acetate, (10E)-13-chloro-10-tridecenyl acetate, (10E)-13-bromo-10-tridecenyl acetate, and (10E)-13-iodo-10-tridecenyl acetate;

14-halo-11-tetradecenyl acetate compounds (a=10) such as (11Z)-14-chloro-11-tetradecenyl acetate, (11Z)-14-bromo-11-tetradecenyl acetate, (11Z)-14-iodin-11-tetradecenyl acetate, (11E)-14-chloro-11-tetradecenyl acetate, (11E)-14-bromo-11-tetradecenyl acetate, and (11E)-14-iodo-11-tetradecenyl acetate;

15-halo-12-pentadecenyl acetate compounds (a=11) such as (127,)-15-chloro-12-pentadecenyl acetate, (12Z)-15-bromo-12-pentadecenyl acetate, (12Z)-15-iodin-12-pentadecenyl acetate, (12E)-15-chloro-12-pentadecenyl acetate, (12E)-15-bromo-12-pentadecenyl acetate, and (12E)-15-iodo-12-pentadecenyl acetate;

16-halo-13-hexadecenyl acetate compounds (a=12) such as (13Z) -16-chloro-13-hexadecenyl acetate, (13Z)-16-bromo-13-hexadecenyl acetate, (13Z)-16-iodo-13-hexadecenyl acetate, (13E)-16-chloro-13-hexadecenyl acetate, (13E)-16-bromo-13-hexadecenyl acetate, and (13E)-16-iodo-13-hexadecenyl acetate;

17-halo-14-heptadecenyl acetate compounds (a=13) such as (14Z)-17-chloro-14-heptadecenyl acetate, (14Z)-17-bromo-14-heptadecenyl acetate, (14Z)-17-iodo-14-heptadecenyl acetate, (14E)-17-chloro-14-heptadecenyl acetate, (14E)-17-bromo-14-heptadecenyl acetate, and (14E)-17-iodo-14-heptadecenyl acetate; and 18-halo-15-octadecenyl acetate compounds (a=14) such as (15Z)-18-chloro-15-octadecenyl acetate, (15Z)-18-bromo-15-octadecenyl acetate, (15Z)-18-iodo-15-octadecenyl acetate, (15E)-18-chloro-15-octadecenyl acetate, (15E)-18-bromo-15-octadecenyl acetate, and (15E)-18-iodo-15-octadecenyl acetate.

Preparation of the Terminal Conjugated Alkadien-1-yl Acetate Compound (5)

The terminal conjugated alkadien-1-yl acetate compound (5) may be prepared by subjecting the haloalkenyl acetate compound (4) to an elimination reaction in the presence of a base, as shown in the following chemical reaction formula.

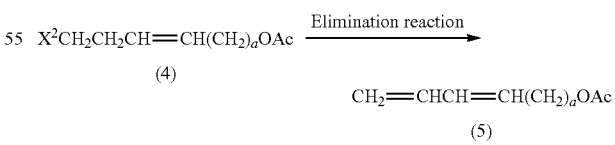

Examples of the base used in the elimination reaction to remove a removing group, $X^2$, include hydroxides such as sodium hydroxide, potassium hydroxide, calcium hydroxide, and magnesium hydroxide; metals alkoxides such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide, and potassium t-amyloxide; organic metal reagents such as methyllithium, ethyllithium, n-butyllithium, methylmagnesium chloride, dimsyl sodium, sodium acetylide, and potassium acetylide; metal amides such as sodium amide, lithium amide, lithium diisopropylamide, lithium hexamethyldisilazide, sodium hexamethyldisilazide, potassium hexamethyldisilazide, and lithium dicyclohexylamide; metal hydride reagents such as sodium hydride, potassium hydride, and calcium hydride; and amines such as triethylamine, N,N-diisopropylethylamine, piperidine, pyrrolidine, pyridine, lutidine, 4-dimethylaminopyridine, N,N-dimethylaniline, N,N-diethylaniline, and 1,8-diazabicyclo[5.4.0]-7-undecene (DBU).

N,N-Diisopropylethylamine, pyridine, and 1,8-diazabicyclo[5.4.0]-7-undecene are preferred as the base in view of the suppression of side reactions and better yield of the terminal conjugated alkadien-1-yl acetate compound (5).

The base may be used alone or in combination thereof, if necessary. The base may be commercially available one.

An amount of the base is preferably 0.8 to 10.0 mol, more preferably 1.0 to 5.0 mol, per mol of the haloalkenyl acetate compound (4) in view of the yield and/or economy.

A solvent may be used in the elimination reaction, if necessary.

Examples of the solvent include usual solvents, for example, ethers such as diethyl ether, dibutyl ether, 4-methyltetrahydropyran, tetrahydrofuran, cyclopentylmethylether, and 1,4-dioxane; hydrocarbons such as hexane, heptane, benzene, toluene, xylene, and cumene; chlorinated solvents such as trichloroethylene, dichloromethane, and chloroform; aprotic polar solvents such as dimethyl sulfoxide, γ-butyrolactone, N-methylpyrrolidone, N,N-dimethylformamide, N,N-dimethylacetamide, and hexamethylphosphoric triamide; nitriles such as acetonitrile and propionitrile; and esters such as methyl acetate, ethyl acetate, n-propyl acetate, and n-butyl acetate. Preferred are ethers such as 4-methyltetrahydropyran and tetrahydrofuran; aprotic polar solvents such as γ-butyrolactone, N-methylpyrrolidone, N,N-dimethylformamide, and N,N-dimethylacetamide; and nitriles such as acetonitrile, more preferably γ-butyrolactone, N-methylpyrrolidone, N,N-dimethylformamide, N,N-dimethylacetamide, and acetonitrile, in view of the reactivity.

The solvent may be used alone or in combination thereof, if necessary. The solvent may be commercially available one.

The base may be used as a solvent without using other solvent.

An amount of the solvent is preferably 0 to 8,000 g, more preferably 0 to 3,000 g, per mol of the haloalkenyl acetate compound (4).

A reaction temperature of the elimination reaction varies, depending on a base to be used, and is preferably −40 to 140° C., more preferably −20 to 100° C., in view of the reactivity.

A reaction time of the elimination reaction varies, depending on a base to be used and/or a reaction scale, and is preferably 1 to 100 hours in view of the reactivity.

The terminal conjugated alkadien-1-yl acetate compound (5) will be explained below.

In the general formula (5), "a" is as defined for the general formula (1), and Ac is as defined for the general formula (3).

Specific examples of the terminal conjugated alkadien-1-yl acetate compound (5) include the following compounds:

4,6-heptadien-1-yl acetate compounds (a=3) such as (4Z)-4,6-heptadien-1-yl acetate and (4E)-4,6-heptadien-1-yl acetate;

5,7-octadien-1-yl acetate compounds (a=4) such as (5Z)-5,7-octadien-1-yl acetate and (5E)-5,7-octadien-1-yl acetate;

6,8-nonadien-1-yl acetate compounds (a=5) such as (6Z)-6,8-nonadien-1-yl acetate and (6E)-6,8-nonadien-1-yl acetate;

7,9-decadien-1-yl acetate compounds (a=6) such as (7Z)-7,9-decadien-1-yl acetate and (7E)-7,9-decadien-1-yl acetate;

8,10-undecadien-1-yl acetate compounds (a=7) such as (8Z)-8,10-undecadien-1-yl acetate and (8E)-8,10-undecadien-1-yl acetate;

9,11-dodecadien-1-yl acetate compounds (a=8) such as (9Z)-9,11-dodecadien-1-yl acetate and (9E)-9,11-dodecadien-1-yl acetate;

10,12-tridecadien-1-yl acetate compounds (a=9) such as (10Z)-10,12-toridecadien-1-yl acetate and (10E)-10,12-toridecadien-1-yl acetate;

11,13-tetradecadien-1-yl acetate compounds (a=10) such as (11Z)-11,13-tetradecadien-1-yl acetate and (11E)-11,13-tetradecadien-1-yl acetate;

12,14-pentadecazien-1-yl acetate compounds (a=11) such as (12Z)-12,14-pentadecadien-1-yl acetate and (12E)-12,14-pentadecadien-1-yl acetate;

13,15-hexadecadien-1-yl acetate compounds (a=12) such as (13Z)-13,15-hexadecadien-1-yl acetate and (13E)-13,15-hexadecadien-1-yl acetate;

14,16-heptadecadien-1-yl acetate compounds (a=13) such as (14Z)-14,16-heptadecadien-1-yl acetate and (14E)-14,16-heptadecadien-1-yl acetate; and 15,17-octadecadien-1-yl acetate compounds (a=14) such as (15Z)-15,17-octadecadien-1-yl acetate and (15E)-15,17-octadecadien-1-yl acetate.

Preparation of the Terminal Conjugated Alkadien-1-ol Compound (6)

The terminal conjugated alkadien-1-ol compound (6) may be prepared by deacetylating the terminal conjugated alkadien-1-yl acetate compound (5), as shown in the following chemical reaction formula.

$$CH_2=CHCH=CH(CH_2)_aOAc \xrightarrow{\text{Deacetylation}}$$
$$(5)$$
$$CH_2=CHCH=CH(CH_2)_aOH$$
$$(6)$$

Examples of the base used in the deacetylation include hydroxides such as sodium hydroxide, potassium hydroxide, calcium hydroxide, and magnesium hydroxide; metal alkoxides such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide, and potassium t-amyloxide; organometallic reagents such as methyllithium, ethyllithium, n-butyllithium, methylmagnesium chloride, dims), sodium acetylide, and potassium acetylide; metal amides such as sodium amide, lithium amide, lithium diisopropylamide, lithium hexamethyldisilazide, sodium hexamethyldisilazide, potassium hexamethyldisilazide, and lithium dicyclohexylamide; metal hydride reagents such as sodium hydride, potassium hydride, and calcium hydride; and amines such as triethylamine, N,N-diisopropylethylamine, piperidine, pyrrolidine, pyridine, lutidine, 4-dimethylaminopyridine, N,N-dimethylaniline, N,N-diethylaniline, and 1,8-diazabicyclo[5.4.0]-7-undecene (DBU).

The deacetylation proceeds in a non-aqueous system, using a base having nucleophilicity such as, for example, metal alkoxides such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide, and potassium t-amyloxide. Meanwhile, when use is made of a base having weak nucleophilicity, for example, hydroxides such as sodium hydroxide, potassium hydroxide, calcium hydroxide, and magnesium hydroxide; and amines such as triethylamine, N,N-diisopropylethylamine, piperidine, pyrrolidine, pyridine, lutidine, 4-dimethylaminopyridine, N,N-dimethylaniline, N,N-diethylaniline, and 1,8-diazabicyclo[5.4.0]-7-undecene (DBU), the deacetylation is carried out using water in addition to the aforesaid base.

Hydroxides such as sodium hydroxide, potassium hydroxide, calcium hydroxide, and magnesium hydroxide are preferred as the base in view of the reactivity and/or economy.

The base may be used alone or in combination thereof, if necessary. The base may be commercially available one.

An amount of the base is preferably 1.0 to 10.0 mol, more preferably 1.0 to 6.0 mol, per mol of the terminal conjugated alkadien-1-yl acetate compound (5) in view of the yield and/or economy.

A solvent may be incorporated in the deacetylation reaction, if necessary.

Examples of the solvent include usual solvents, for example, alcohols such as methanol, ethanol, n-propanol, n-butanol, isopropanol, 2-butanol, ethyleneglycol, propyleneglycol, 2-methyl-1,3-propanediol, 2,2-dimethyl-1,3-propanediol, 1,2-dimethyl-1,3-propanediol, 1,3-dimethyl-1,3-propanediol, and 2-methyl-1,4-butanediol; ethers such as diethyl ether, dibutyl ether, 4-methyltetrahydropyran, tetrahydrofuran, cyclopentylmethylether, and 1,4-dioxane; hydrocarbons such as hexane, heptane, benzene, toluene, xylene, and cumene; chlorinated solvents such as trichloroethylene, dichloromethane, and chloroform; aprotic polar solvents such as dimethyl sulfoxide, γ-butyrolactone, N-methylpyrrolidone, N,N-dimethylformamide, N,N-dimethylacetamide, and hexamethylphosphoric triamide; nitriles such as acetonitrile and propionitrile; and esters such as methyl acetate, ethyl acetate, n-propyl acetate, and n-butyl acetate. An optimum solvent depends on a base used. When a metal alkoxide is used as the base, preferable are ethers such as tetrahydrofuran; aprotic polar solvents such as γ-butyrolactone, N-methylpyrrolidone, N,N-dimethylformamide, and N,N-dimethylacetamide. When a hydroxide is used as the base, alcohols such as methanol and ethanol are preferable.

The solvent may be used alone or in combination thereof, if necessary. The solvent may be commercially available one.

An amount of the solvent used in the deacetylation is preferably 0 to 8,000 g, more preferably 0 to 3,000 g, per mol of the terminal conjugated alkadien-1-yl acetate compound (5).

A reaction temperature of the deacetylation varies, depending on a base to be used, and is preferably −40 to 140° C., more preferably −20 to 100° C., in view of the reactivity.

A reaction time of the deacetylation varies, depending on a base to be used and/or a reaction scale, and is preferably 1 to 100 hours in view of the reactivity.

Further, the terminal conjugated alkadien-1-ol compound (6) may be prepared by deacetylating the haloalkenyl acetate compound (4) in the presence of a base in parallel with the elimination reaction, as shown in the following chemical reaction formula (see the Example 12 below).

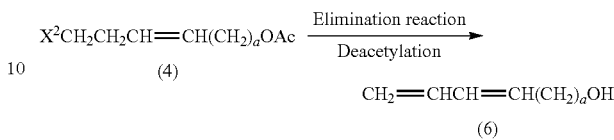

Examples of the base used in the elimination reaction and the deacetylation include hydroxides such as sodium hydroxide, potassium hydroxide, calcium hydroxide, and magnesium hydroxide; metal alkoxides such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide, and potassium t-amyloxide; organometallic reagents as methyllithium, ethyllithium, n-butyllithium, methylmagnesium chloride, dimsyl sodium, sodium acetylide, and potassium acetylide; metal amides such as sodium amide, lithium amide, lithium diisopropylamide, lithium hexamethyldisilazide, sodium hexamethyldisilazide, potassium hexamethyldisilazide, and lithium dicyclohexylamide; metal hydride reagents such as sodium hydride, potassium hydride, and calcium hydride; and amines such as triethylamine, N,N-diisopropylethylamine, piperidine, pyrrolidine, pyridine, lutidine, 4-dimethylaminopyridine, N,N-dimethylaniline, N,N-diethylaniline, and 1,8-diazabicyclo[5.4.0]-7-undecene (DBU).

The elimination reaction and the deacetylation proceed in a non-aqueous system, using a base having nucleophilicity such as, for example, metal alkoxides such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide, and potassium t-amyloxide. Meanwhile, when use is made of a base having weak nucleophilicity, for example, hydroxides such as sodium hydroxide, potassium hydroxide, calcium hydroxide, and magnesium hydroxide; and amines such as triethylamine, N,N-diisopropylethylamine, piperidine, pyrrolidine, pyridine, lutidine, 4-dimethylaminopyridine, N,N-dimethylaniline, N,N-diethylaniline, and 1,8-diazabicyclo[5.4.0]-7-undecene (DBU), the elimination reaction and the deacetylation proceed in parallel using water in addition to the aforesaid base.

Metal alkoxides such as sodium methoxide, sodium ethoxide, sodium t-butoxide, and potassium t-butoxide are preferred as the base in view of the suppression of side reactions and better yield of the terminal conjugated alkadien-1-ol compound (5).

The base may be used alone or in combination thereof, if necessary. The base may be commercially available one.

An amount of the base is preferably 0.8 to 15.0 mol, more preferably 1.0 to 8.0 mol, per mol of the haloalkenyl acetate compound (4) in view of the yield and/or economy.

When the elimination reaction and the deacetylation are carried out in parallel, a solvent may be incorporated in the elimination reaction and the deacetylation, if necessary.

Examples of the solvent include usual solvents, for example, ethers such as diethyl ether, dibutyl ether, 4-methyltetrahydropyran, tetrahydrofuran, cyclopentylmethylether, and 1,4-dioxane; hydrocarbons such as hexane, heptane, benzene, toluene, xylene, and cumene; chlorinated solvents such as trichloroethylene, dichloromethane, and chloroform; aprotic polar solvents such as dimethyl sulfoxide, γ-butyrolactone, N-methylpyrrolidone, N,N-dimethylformamide, N,N-dimethylacetamide, and hexamethylphosphoric triamide; nitriles such as acetonitrile and propionitrile; and esters such as methyl acetate, ethyl acetate, n-propyl acetate, and n-butyl acetate. Preferred are ethers such as 4-methyltetrahydropyran and tetrahydrofuran; aprotic polar solvents such as γ-butyrolactone, N-methylpyrrolidone, N,N-dimethylformamide, and N,N-dimethylacetamide; and nitriles such as acetonitrile, more preferably tetrahydrofuran, 4-methyltetrahydropyran, γ-butyrolactone, N-methylpyrrolidone, N,N-dimethylformamide, N,N-dimethylacetamide, and acetonitrile, in view of the reactivity.

The solvent may be used alone or in combination thereof, if necessary. The solvent may be commercially available one.

An amount of the solvent used in the deacetylation is preferably 0 to 8,000 g, more preferably 0 to 3,000 g, per mol of the haloalkenyl acetate compound (4).

When the elimination reaction and the deacetylation are carried out in parallel, a reaction temperature varies, depending on a base to be used, and is preferably −40 to 140° C., more preferably −20 to 100° C., in view of the reactivity.

When the elimination reaction and the deacetylation are carried out in parallel, a reaction time varies, depending on a base to be used and/or a reaction scale, and is preferably 1 to 100 hours in view of the reactivity.

The terminal conjugated alkadien-1-ol compound (6) will be explained below.

"a" in the general formula (6) is as defined for the general formula (1).

Specific examples of the terminal conjugated alkadien-1-ol compound (6) include the following compounds:

4,6-heptadien-1-ol compounds (a=3) such as (4Z)-4,6-heptadien-1-ol and (4E)-4,6-heptadien-1-ol;

5,7-octadien-1-ol compounds (a=4) such as (5Z)-5,7-octadien-1-ol and (5E)-5,7-octadien-1-ol;

6,8-nonadien-1-ol compounds (a=5) such as (6Z)-6,8-nonadien-1-ol and (6E)-6,8-nonadien-1-ol;

7,9-decadien-1-ol compounds (a=6) such as (7Z)-7,9-decadien-1-ol and (7E)-7,9-decadien-1-ol;

8,10-undecadien-1-ol compounds (a=7) such as (8Z)-8,10-undecadien-1-ol and (8E)-8,10-undecadien-1-ol;

9,11-dodecadien-1-ol compounds (a=8) such as (9Z)-9,11-dodecadien-1-ol and (9E)-9,11-dodecadien-1-ol;

10,12-tridecadien-1-ol compounds (a=9) such as (10Z)-10,12-tridecadien-1-ol and (10E)-10,12-tridecadien-1-ol;

11,13-tetradecadien-1-ol compounds (a=10) such as (11Z)-11,13-tetradecadien-1-ol and (11E)-11,13-tetradecadien-1-ol;

12,14-pentadecadien-1-ol compounds (a=11) such as (12Z)-12,14-pentadecadien-1-ol and (12E)-12,14-pentadecadien-1-ol;

13,15-hexadecadien-1-ol compounds (a=12) such as (13Z)-13,15-hexadecadien-1-of and (13E)-13,15-hexadecadien-1-ol;

14,16-heptadecadien-1-ol compounds (a=13) such as (14Z)-14,16-heptadecadien-1-ol and (14E)-14,16-heptadecadien-1-ol; and 15,17-octadecadien-1-ol compounds (a=14) such as (15Z)-15,17-octadecadien-1-ol and (15E)-15,17-octadecadien-1-ol.

EXAMPLES

The present invention will be described with reference to the following Examples. It should be noted that the present invention is not limited to or by the Examples.

The term "purity" as used herein means an area percentage in gas chromatography (GC), unless otherwise specified. The term "production ratio" means a ratio of area percentages in GC. The term "yield" is calculated from the area percentages determined by GC.

In the Examples, monitoring of the reactions and calculation of the yields were carried out in the following GC conditions.

GC conditions: GC: Capillary gas chromatograph GC-2014 (Shimadzu Corporation); column: DB-WAX (sp-2331), 0.25 μm×0.25 mmφ×30 m; carrier gas: He (1.55 mL/min), detector: FID; column temperature: 150° C., elevated in a rate of 5° C./min, and up to 230° C.

The yield was calculated according to the following equation in consideration of purities (% GC) of a starting material and a product.

Yield (%)={[(weight of a product obtained by a reaction×% GC)/molecular weight of a product]÷[(weight of a starting material in a reaction×% GC)/molecular weight of a starting material]}×100

THF represents tetrahydrofuran, DMAC represents N,N-dimethylacetamide, DMF represents N,N-dimethylformamide, GBL represents γ-butyrolactone, DBU represents 1,8-diazabicydo[5.4.0]-7-undecene, $^t$Bu represents a tert-butyl group, and Ph represents a phenyl group.

Example 1: Preparation of (3Z)-10-bromo-3-decenyl Methoxymethyl Ether (1: $R^1$=H, $X^1$=Br; a=6)

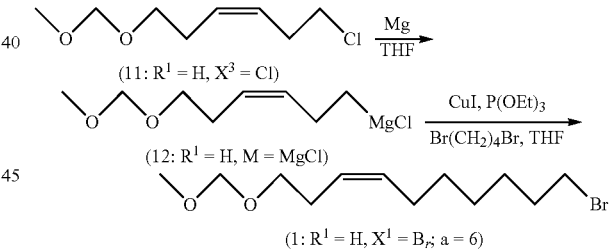

Magnesium (26.73 g, 1.1 gram atoms) and tetrahydrofuran (300.00 g) were placed in a reactor at room temperature and stirred at 60 to 65° C. for 29 minutes. After the completion of the stirring, (3Z)-6-chloro-3-hexene methoxymethyl ether (11: $R^1$=H, $X^3$=Cl) (184.15 g, 1.00 mol, purity 97.02%) was added dropwise to the reactor at 60 to 75° C. After the completion of the dropwise addition, the reaction mixture was stirred at 75 to 80° C. for 2 hours to obtain (3Z)-6-(methoxymethoxy)-3-hexenylmagnesium chloride (12: $R^1$=H, M=MgCl).

Subsequently, cuprous iodide (1.00 g, 0.0053 mol), triethyl phosphite (1.00 g, 0.0060 mol), tetrahydrofuran (389.20 g), and 1,4-dibromobutane (431.84 g, 2.00 mol) were added to another reactor, and then the (3Z)-6-(methoxymethoxy)-3-hexenylmagnesium chloride (12: $R^1$=H, M=MgCl) obtained above was added dropwise at −5 to 15° C. After the completion of the dropwise addition, the reaction mixture was stirred at 5 to 15° C. for 3.5 hours.

After the completion of the-stirring, an aqueous ammonium chloride solution (ammonium chloride (21.83 g) and water (455.87 g), and subsequently acetic acid (102.56 g) were added, followed by phase separation. The aqueous phase was removed to obtain the organic phase. The organic phase thus obtained was concentrated at a reduced pressure, and the concentrate was subjected to distillation at a reduced pressure to obtain (3Z)-10-bromo-3-decenyl methoxymethyl ether (1: $R^1$=H, $X^1$=Br; a=6) (230.57 g, 0.79 mol, purity 95.70%, b.p.=124.1 to 130.0° C./0.40 kPa (3.0 mmHg)) in a yield of 79.03%.

The following is the spectrum data of the (3Z)-10-bromo-3-decenyl methoxymethyl ether (1: $R^1$=H, $X^1$=Br; a=6) thus prepared.

Nuclear magnetic resonance spectrum: $^1$H-NMR (500 MHz, CDCl$_3$): δ=1.27-1.46 (6H, m), 1.84 (2H, quin-like, J=7.3 Hz), 2.05 (2H, dt, J=6.9 Hz, 6.9 Hz), 2.33 (2H, dt, J=6.9 Hz, 6.9 Hz), 3.35 (3H, s), 3.39 (2H, t, J=6.9 Hz), 3.52 (2H, t, J=6.9 Hz), 4.62 (2H, s), 5.38 (1H, dtt, J=11.1 Hz, 6.9 Hz, 1.5 Hz), 5.46 (1H, dtt, J=10.7 Hz, 6.9 Hz, 1.5 Hz); $^{13}$C-NMR (500 MHz, CDCl$_3$): δ=27.14, 27.87, 27.99, 28.32, 29.31, 32.72, 33.90, 55.10, 67.34, 96.31, 125.66, 131.79.

Mass spectrum: EI-mass spectrum (70 eV): m/z 277 (M$^+$–1), 247, 216, 190, 176, 162, 148, 123, 109, 95, 81, 67, 45.

Infrared absorption spectrum (D-ATR): νmax=2929, 2856, 1464, 1440, 1213, 1150, 1111, 1072, 1035, 919, 727.

Example 2: Preparation of
(3Z)-11-chloro-3-undecenyl Methoxymethyl Ether
(1: $R^1$=H, $X^1$=Cl; a=7)

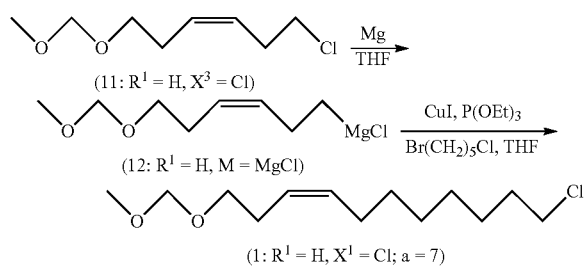

Magnesium (53.05 g, 2.18 gram atoms) and tetrahydrofuran (623.70 g) were placed in a reactor at room temperature and stirred at 60 to 65° C. for 16 minutes. After the completion of the stirring, (3Z)-6-chloro-3-hexene methoxymethyl ether (11: $R^1$=H, $X^3$=Cl) (381.66 g, 2.08 mol, purity 97.33%) was added dropwise to the reactor at 60 to 75° C. After the completion of the dropwise addition, the reaction mixture was stirred at 75 to 80° C. for 2 hours to obtain (3Z)-6-(methoxymethoxy)-3-hexenylmagnesium chloride (12: $R^1$=H, M=MgCl).

Subsequently, cuprous iodide (3.96 g, 0.021 mol), triethyl phosphite (8.29 g, 0.050 mol), tetrahydrofuran (207.90 g), and 1-bromo-5-chloropentane (358.64 g, 1.93 mol) were added to another reactor, and then the (3Z)-6-(methoxymethoxy)-3-hexenylmagnesium chloride (12: $R^1$=H, M=MgCl) obtained above was added dropwise at −5 to 15° C. After the completion of the dropwise addition, the reaction mixture was stirred at 5 to 15° C. for 4 hours. After the completion of the stirring, an aqueous acetic acid solution (acetic acid (259.88 g) and water (779.63 g)) were added to the reaction mixture, followed by phase separation. The aqueous phase was removed to obtain the organic phase.

The organic phase thus obtained was concentrated at a reduced pressure, and the concentrate was subjected to distillation at a reduced pressure to obtain (3Z)-11-chloro-3-undecenyl methoxymethyl ether (1: $R^1$=H, $X^1$=Cl; a=7) (465.53 g, 1.80 mol, purity 96.25%, b.p.=134.1 to 142.2° C./0.40 kPa (3.0 mmHg)) in a yield of 93.19%.

The following is the spectrum data of the (3Z)-11-chloro-3-undecenyl methoxymethyl ether (1: $R^1$=H, $X^1$=Cl; a=7) thus prepared.

Nuclear magnetic resonance spectrum: $^1$H-NMR (500 MHz, CDCl$_3$): δ=1.26-1.45 (8H, m), 1.75 (2H, quin-like, J=7.3 Hz), 2.04 (2H, dt, J=6.9 Hz, 6.9 Hz), 2.33 (2H, dt, J=6.9 Hz, 6.9 Hz), 3.35 (3H, s), 3.50-3.54 (4H, m), 4.62 (2H, s), 5.38 (1H, dtt, J=10.7 Hz, 6.9 Hz, 1.6 Hz), 5.46 (1H, dtt, J=11.1 Hz, 7.3 Hz, 1.6 Hz); $^{13}$C-NMR (500 MHz, CDCl$_3$): δ=26.79, 27.23, 27.86, 28.72, 29.01, 29.42, 32.56, 45.08, 55.09, 67.35, 96.30, 125.50, 131.96.

Mass spectrum: EI-mass spectrum (70 eV): m/z 247 (M$^+$–1), 217, 186, 165, 144, 118, 95, 68, 45.

Infrared absorption spectrum (D-ATR): νmax=2929, 2856, 1465, 1150, 1111, 1073, 1036, 919, 726, 652.

Example 3: Preparation of
(3E)-11-chloro-3-undecenyl methoxymethyl ether
(1: $R^1$=H, $X^1$=Cl; a=7)

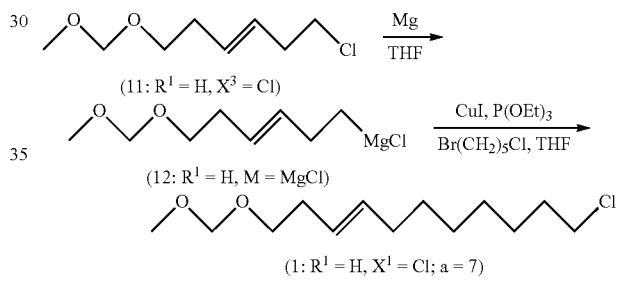

Magnesium (25.52 g, 1.05 gram atoms) and tetrahydrofuran (300.00 g) were placed in a reactor at room temperature and stirred at 60 to 65° C. for 20 minutes. After the completion of the stirring, (3E)-6-chloro-3-hexene methoxymethyl ether (11: $R^1$=H, $X^3$=Cl) (183.02 g, 1.00 mol, purity 97.62%) was added dropwise to the reactor at 60 to 75° C. After the completion of the dropwise addition, the reaction mixture was stirred at 75 to 80° C. for 2 hours to obtain (3E)-6-(methoxymethoxy)-3-hexenylmagnesium chloride (12: $R^1$=H, M=MgCl).

Subsequently, cuprous iodide (1.90 g, 0.010 mol), triethyl phosphite (3.99 g, 0.024 mol), tetrahydrofuran (100.00 g), and 1-bromo-5-chloropentane (172.51 g, 0.93 mol) were added to another reactor, and then the (3E)-6-(methoxymethoxy)-3-hexenylmagnesium chloride (12: $R^1$=H, M=MgCl) obtained above was added dropwise at −5 to 15° C. After the completion of the dropwise addition, the reaction mixture was stirred at 5 to 15° C. for 4 hours. After the completion of the stirring, an aqueous acetic acid solution (acetic acid (125.00 g) and water (375.00 g)) were added to the reaction mixture, followed by phase separation. The aqueous phase was removed to obtain the organic phase. The organic phase thus obtained was concentrated at a reduced pressure, and the concentrate was subjected to distillation at a reduced pressure to obtain (3E)-11-chloro-3-undecenyl methoxymethyl ether (1: $R^1$=H, $X^1$=Cl; a=7)

(224.30 g, 0.88 mol, purity 98.11%, b.p.=139.1 to 145.0° C./0.40 kPa (3.0 mmHg)) in a yield of 95.11%.

The following is the spectrum data of the (3E)-11-chloro-3-undecenyl methoxymethyl ether (1: $R^1$=H, $X^1$=Cl; a=7) thus prepared.

Nuclear magnetic resonance spectrum: $^1$H-NMR (500 MHz, CDCl$_3$): δ=1.24-1.46 (8H, m), 1.75 (2H, quin-like, J=6.9 Hz), 1.98 (2H, dt, J=6.9 Hz, 6.9 Hz), 2 .28 (2H, ddt, J=1.1 Hz, 6.7 Hz, 6.7 Hz), 3.35 (3H, s), 3.52 (4H, q-like, J=6.9 Hz), 4.61 (2H, s), 5.35-5.44 (1H, m), 5.45-5.54 (1H, m); $^{13}$C-NMR (500 MHz, CDCl$_3$): δ=26.79, 28.69, 28.89, 29.24, 32.52, 32.58, 33.01, 45.09, 55.08, 67.61, 96.32, 126.26, 132.55.

Mass spectrum: EI-mass spectrum (70 eV): m/z 247 ($M^+$–1), 217, 186, 158, 144, 109, 95, 82, 68, 45.

Infrared absorption spectrum (D-ATR): νmax=2928, 2856, 1465, 1443, 1150, 1111, 1072, 1041, 968, 919, 726, 652.

Example 4: Preparation of (3Z)-14-chloro-3-tetradecenyl Methoxymethyl Ether (1: $R^1$=H, $X^1$=Cl; a=10)

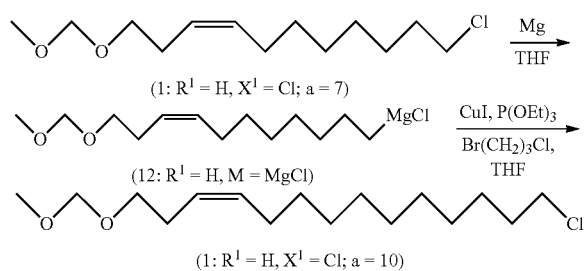

Magnesium (13.37 g, 0.55 gram atom) and tetrahydrofuran (150.00 g) were placed in a reactor at room temperature and stirred at 60 to 65° C. for 39 minutes. After the completion of the stirring, (3Z)-11-chloro-3-undecenyl methoxymethyl ether (1: $R^1$=H, $X^1$=Cl; a=7) (130.82 g, 0.50 mol, purity 95.09%) was added dropwise to the reactor at 60 to 75° C. After the completion of the dropwise addition, the reaction mixture was stirred at 75 to 80° C. for 2 hours to obtain (8Z)-11-(methoxymethoxy)-8-undecenylmagnesium chloride (12: $R^1$=H, M=MgCl).

Subsequently, cuprous iodide (0.95 g, 0.0050 mol), triethyl phosphite (1.99 g, 0.012 mol), tetrahydrofuran (50.00 g), and 1-bromo-3-chloropropane (73.21 g, 0.47 mol) were added to another reactor, and then the (8Z)-11-(methoxymethoxy)-8-undecenylmagnesium chloride (12: $R^1$=H, M=MgCl) obtained above was added dropwise at −5 to 15° C. After the completion of the dropwise addition, the reaction mixture was stirred at 5 to 15° C. for 2.5 hours. After the completion of the stirring, an aqueous ammonium chloride solution (ammonium chloride (5.27 g) and water (136.06 g)), and subsequently acetic acid (51.28 g), were added to the reaction mixture, followed by phase separation. The aqueous phase was removed to obtain the organic phase. The organic phase thus obtained was concentrated at a reduced pressure, and the concentrate was subjected to distillation at a reduced pressure to obtain (3Z)-14-chloro-3-tetradecenyl methoxymethyl ether (1: $R^1$=H, $X^1$=Cl; a=10) (122.32 g, 0.39 mol, purity 92.00%, b.p.=130.0 to 146.1° C./0.40 kPa (3.0 mmHg)) in a yield of 83.20%.

The following is the spectrum data of the (3Z)-14-chloro-3-tetradecenyl methoxymethyl ether (1: $R^1$=H, $X^1$=Cl; a=10) thus prepared.

Nuclear magnetic resonance spectrum: $^1$H-NMR (500 MHz, CDCl$_3$): δ=1.23-1.37 (12H, m), 1.37-1.45 (2H, m), 1.76 (2H, quin-like, J=6.9 Hz), 2.04 (2H, dt, J=6.9 Hz, 6.9 Hz), 2.34 (2H, dt, J=7.1 Hz, 7.1 Hz), 3.35 (3H, s), 3.52 (4H, dt, J=6.9 Hz, 3.1 Hz), 4.62 (2H, s), 5.37 (1H, dtt, J=11.1 Hz, 7.3 Hz, 1.5 Hz), 5.47 (1H, dtt, J=10.7 Hz, 7.3 Hz, 1.5 Hz); $^{13}$C-NMR (500 MHz, CDCl$_3$): δ=26.85, 27.31, 27.87, 28.85, 29.22, 29.41, 29.44, 29.46, 29.57, 32.62, 45.13, 55.09, 67.39, 96.31, 125.36, 132.14.

Mass spectrum: EI-mass spectrum (70 eV): m/z 289 ($M^+$–1), 259, 228, 214, 200, 186, 172, 158, 110, 96, 82, 68.

Infrared absorption spectrum (D-ATR): νmax=2926, 2854, 1465, 1150, 1111, 1036, 920, 724.

Example 5: Preparation of (3Z)-11-iodo-3-undecenyl Methoxymethyl Ether (1: $R^1$=H, $X^1$=I; a=7)

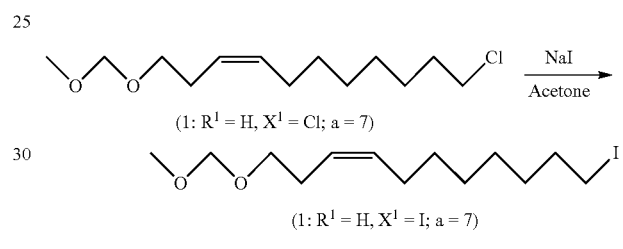

(3Z)-11-Chloro-3-undecenyl methoxymethyl ether (1: $R^1$=H, $X^1$=Cl; a=7) (10.00 g, 0.038 mol, purity 95.09%) obtained as in Example 2, sodium iodide (28.45 g, 0.19 mol) and acetone (191.10 g) were placed in a reactor at room temperature and stirred at 55 to 60° C. for 23 hours. After the completion of the stirring, water (200.00 g) and subsequently hexane (200.00 g) were added to the reaction mixture, followed by phase separation. The aqueous phase was removed to obtain the organic phase. The organic phase thus obtained was concentrated at a reduced pressure, and the concentrate was purified by column chromatography (ethyl acetate/n-hexane=50/1) to obtain (3Z)-11-iodo-3-undecenyl methoxymethyl ether (1: $R^1$=H, $X^1$=I; a=7) (12.05 g, 0.032 mol, purity 91.23%) in a yield of 84.52%.

The following is the spectrum data of the (3Z)-11-iodo-3-undecenyl methoxymethyl ether (1: $R^1$=H, $X^1$=I; a=7) thus prepared.

Nuclear magnetic resonance spectrum: $^1$H-NMR (500 MHz, CDCl$_3$): δ=1.25-1.44 (8H, m), 1.81 (2H, quin-like, J=7.3 Hz), 2.04 (2H, dt, J=6.9 Hz, 6.9 Hz), 2.34 (2H, dt, J=6.9 Hz, 6.9 Hz), 3.18 (2H, t, J=6.9 Hz), 3.35 (3H, s), 3.52 (2H, t, J=6.9 Hz), 4.62 (2H, s), 5.38 (1H, dtt, J=10.7 Hz, 7.3 Hz, 1.2 Hz), 5.46 (1H, dtt, J=11.1 Hz, 7.3 Hz, 1.6 Hz); $^{13}$C-NMR (500 MHz, CDCl$_3$): δ=7.19, 27.23, 27.89, 28.38, 28.98, 29.43, 30.41, 33.49, 55.11, 67.38, 96.32, 125.52, 131.96.

Mass spectrum: EI-mass spectrum (70 eV): m/z 339 ($M^+$–1), 309, 278, 252, 196, 180, 95, 69, 45.

Infrared absorption spectrum (D-ATR): νmax=2927, 2854, 1464, 1150, 1111, 1035, 919, 722.

Example 6: Preparation of (3Z)-11-chloro-3-undecenyl Butoxymethyl Ether (1: $R^1$=$CH_3CH_2CH_2$, $X^1$=Cl; a=7)

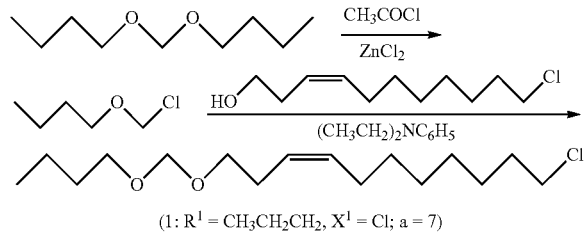

(1: $R^1$ = $CH_3CH_2CH_2$, $X^1$ = Cl; a = 7)

Zinc chloride (0.038 g, 0.28 mmol) and dibutoxymethane (7.57 g, 0.046 mol, purity 98.00%) were placed in a reactor at room temperature and stirred at 15 to 25° C. for 12 minutes. After the completion of the stirring, acetyl chloride (3.30 g, 0.042 mol) was added dropwise at 20 to 35° C. After the completion of the dropwise addition, the reaction mixture was stirred at 35 to 40° C. for 2 hours to obtain chloromethyl butyl ether.

Subsequently, a mixture solution of (3Z)-11-chloro-3-undecen-1-ol (2: $X^1$=Cl; a=7) (6.00 g, 0.028 mol, purity 95.73%) and N,N-diethylaniline (6.27 g, 0.042 mol) was added dropwise to the reactor at 20 to 30° C. and stirred at 20 to 30° C. for 6 hours. After the completion of the stirring, an aqueous 25% by mass sodium hydroxide solution (10.00 g, 0.063 mol as sodium hydroxide) and subsequently water (15.00 g) were added to the reaction mixture, followed by phase separation. The aqueous phase was removed to obtain the organic phase. The organic phase thus obtained was concentrated at a reduced pressure, and the concentrate was subjected to distillation at a reduced pressure to obtain (3Z)-11-chloro-3-undecenyl butoxymethyl ether (1: $R^1$=$CH_3CH_2CH_2$, $X^1$=Cl; a=7) (7.49 g, 0.023 mol, purity 89.10%) in a yield of 82.84%.

The following is the spectrum data of the (3Z)-11-chloro-3-undecenyl butoxymethyl ether (1: $R^1$=$CH_3CH_2CH_2$, $X^1$=Cl; a=7) thus prepared.

Nuclear magnetic resonance spectrum: $^1$H-NMR (500 MHz, $CDCl_3$): δ=0.92 (3H, t, J=7.3 Hz), 1.26-1.46 (10H, m), 1.53-1.60 (2H, m), 1.76 (2H, quin-like, J=7.3 Hz), 2.04 (2H, dt, J=6.9 Hz, 6.9 Hz), 2.33 (2H, dt, J=7.1 Hz, 7.1 Hz), 3.50-3.55 (6H, m), 4.66 (2H, s), 5.38 (1H, dtt, J=11.1 Hz, 7.3 Hz, 1.6 Hz), 5.46 (1H, dtt, J)=11.1 Hz, 7.3 Hz, 1.5 Hz); $^{13}$C-NMR (500 MHz, $CDCl_3$): δ=13.85, 19.36, 26.81, 27.25, 27.89, 28.74, 29.04, 29.45, 31.79, 32.59, 45.08, 67.33, 67.55, 95.17, 125.57, 131.93.

Mass spectrum: EI-mass spectrum (70 eV): m/z 289 ($M^+$–1), 217, 186, 172, 158, 144, 87, 57.

Infrared absorption spectrum (D-ATR): νmax=2930, 2858, 1464, 1379, 1116, 1074, 1040, 727.

Example 7: Preparation of (3Z)-11-chloro-3-undecenyl Benzyloxymethyl Ether (1: $R^1$=Ph, $X^1$=Cl; a=7)

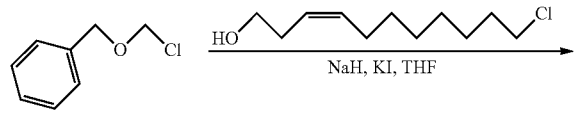

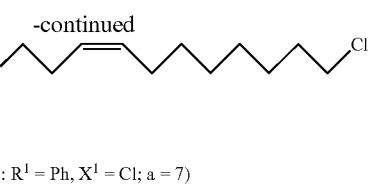

(1: $R^1$ = Ph, $X^1$ = Cl; a = 7)

Sodium hydride (0.90 g, 0.021 mmol, purity 55%), potassium iodide (0.031 g, 0.19 mmol) and tetrahydrofuran (30.00 g) were placed in a reactor at room temperature and stirred at 0 to 5° C. for 10 minutes. After the completion of the stirring, (3Z)-11-chloro-3-undecen-1-ol (2: $X^1$=Cl; a=7) (4.00 g, 0.019 mol, purity 95.73%) was added dropwise at 0 to 10° C. and stirred at 45 to 55° C. for 3 hours. Subsequently, water (59.00 g) was added to the reaction mixture, followed by phase separation. The aqueous phase was removed to obtain the organic phase. The organic phase thus obtained was concentrated at a reduced pressure, and the concentrate was purified by column chromatography (ethyl acetate/n-hexane=20/1) to obtain (3Z)-11-chloro-3-undecenyl benzyloxymethyl ether (1: $R^1$=Ph, $X^1$=Cl; a=7) (0.78 g, 0.0020 mol, purity 83.50%) in a yield of 10.72%.

The following is the spectrum data of the (3Z)-11-chloro-3-undecenyl benzyloxymethyl ether (1: $R^1$=Ph, $X^1$=Cl; a=7) thus prepared.

Nuclear magnetic resonance spectrum: $^1$H-NMR (500 MHz, $CDCl_3$): δ=1.28-1.39 (6H, m), 1.39-1.47 (2H, m), 1.73-1.81 (2H, m), 2.06 (2H, dt, J=6.9 Hz, 6.9 Hz), 2.36 (2H, q-like, J=6.9 Hz), 3.53 (2H, t, J=6.9 Hz), 3.61 (2H, t, J=6.9 Hz), 4.62 (2H, s), 4.77 (2H, s), 5.41 (1H, dtt, J=10.7 Hz, 7.3 Hz, 1.2 Hz), 5.49 (1H, dtt, J=10.7 Hz, 7.3 Hz, 1.5 Hz), 7.34-7.38 (5H, m); $^{13}$C-NMR (500 MHz, $CDCl_3$): δ=26.80, 27.26, 27.86, 28.74, 29.04, 29.44, 32.57, 45.09, 67.58, 69.26, 94.51, 125.52, 127. 63, 127.69, 127.85, 127.92, 128.37, 128.40, 132.02.

Mass spectrum: EI-mass spectrum (70 eV): m/z 324 ($M^+$–1), 217, 186, 137, 121, 91.

Infrared absorption spectrum (D-ATR): νmax=2929, 2856, 1455, 1378, 1113, 1041, 1028, 735, 698, 651.

Example 8: Preparation of (3Z)-10-bromo-3-decen-1-ol (2: $X^1$=Br; a=6)

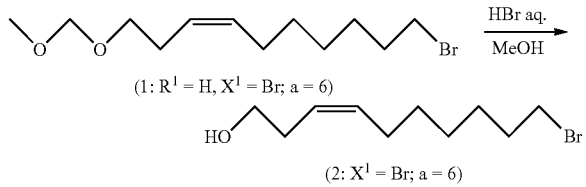

(3Z)-10-Bromo-3-decenyl methoxymethyl ether (1: $R^1$=H, $X^1$=Br; a=6) (60.00 g, 0.21 mol, purity 95.70%) obtained as in Example 1, methanol (102.85 g, 3.21 mol) and 20% by mass hydrobromic acid (21.65 g, 0.053 mol as hydrogen bromide) were placed in a reactor equipped with a distillation column, and the reaction mixture was raised to 60° C. and stirred for 3 hours. After the completion of the stirring, the internal temperature was raised to 65 to 70° C., and a mixture of dimethoxymethane and methanol by-produced was distilled off from the distillation column. The reaction mixture during the reaction was sampled, and when the reaction rate reached 100%, water (300.00 g) was added, followed by phase separation. The aqueous phase was removed to obtain the organic phase. The organic phase thus obtained was-concentrated at a reduced pressure, and the concentrate was subjected to distillation at a reduced pressure to obtain (3Z)-10-bromo-3-decen-1-ol (2: $X^1$=Br; a=6) (48.69 g, 0.19 mol, purity 91.00%, b.p.=119.0 to 121.1° C./0.40 kPa (3.0 mmHg)) in a yield of 91.57%.

The following is the spectrum data of the (3Z)-10-bromo-3-decen-1-ol (2: $X^1$=Br; a=6) thus prepared.

Nuclear magnetic resonance spectrum: $^1$H-NMR (500 MHz, CDCl$_3$): δ=1.27-1.47 (6H, m), 1.59 (1H, br.s), 1.84 (2H, quin-like, J=6.9 Hz), 2.06 (2H, dt, J=6.9 Hz, 6.9 Hz), 2.32 (2H, dt, J=6.9 Hz, 6.9 Hz), 3.39 (2H, t, J=6.9 Hz), 3.63 (2H) , t, J=6.5 Hz), 5.36 (1H, dtt, J =10.7 Hz, 7.3 Hz, 1.5 Hz), 5.53 (1H, dtt, J=11.1 Hz, 7.3 Hz, 1.5 Hz); $^{13}$C-NMR (500 MHz, CDCl$_3$): δ=27.16, 27.97, 28.32, 29.38, 30.76, 32.70, 33.92, 62.25, 125.22, 133.06.

Mass spectrum: EI-mass spectrum (70 eV): m/z 233 ($M^+$–1), 216, 190, 137, 123, 109, 95, 81, 67, 55, 41.

Infrared absorption spectrum (D-ATR): νmax=3333, 2930, 2855, 1462, 1437, 1048, 726, 645, 562.

Example 9: Preparation of (7Z)-10-hydroxy-7-decenyl Acetate (3: a=6)

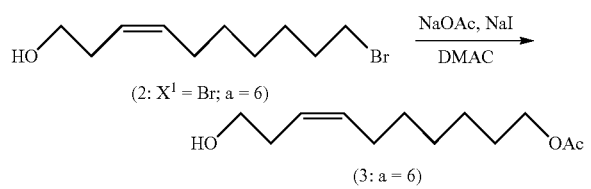

(3Z)-10-Bromo-3-decen-1-ol (2: $X^1$=Br; a=6) (29.56 g, 0.11 mol, purity 91.00%) obtained in Example 8, sodium acetate (16.89 g, 0.21 mol), sodium iodide (1.14 g, 0.0076 mol) and DMAC (114.40 g) were placed in a reactor at room temperature and stirred at 125 to 135° C. for 3.5 hours. After cooling to 50 to 60° C., water (150.00 g) was added to the reaction mixture, followed by phase separation. The aqueous phase was removed to obtain the organic phase. The organic phase thus obtained was concentrated at a reduced pressure, and the residue was purified by column chromatography (ethyl acetate/n-hexane=5/1) to obtain (7Z)-10-hydroxy-7-decenyl acetate (3: a=6) (19.63 g, 0.086 mol, purity 93.73%) in a yield of 75.06%.

The following is the spectrum data of the (7Z)-10-hydroxy-7-decenyl acetate (3: a=6) thus prepared.

Nuclear magnetic resonance spectrum: $^1$H-NMR (500 MHz, CDCl$_3$): δ32 1.25-1.39 (6H, m), 1.60 (2H, quin-like, J=6.9 Hz), 1.72 (1H, br.s), 2.02 (3H, s), 2.04 (2H, q-like, J=6.5 Hz), 2.30 (2H, q-like, J=6.9 Hz), 3.61 (2H, t, J=6.5 Hz), 4 .03 (2H, t, J=6.9 Hz), 5.35 (1H, dtt, J=11.1 Hz, 7.3 Hz, 1.5 Hz), 5.52 (1H, dtt, J=10.7 Hz, 7.3 Hz, 1.5 Hz); $^{13}$C-NMR (500 MHz, CDCl$_3$): δ=20.93, 25.69, 27.15, 28.47, 28.76, 29.42, 30.74, 62.22, 64.52, 125.19, 133.00, 171.23.

Mass spectrum: EI-mass spectrum (70 eV): m/z 196 ($M^+$–18), 124, 107, 95, 81, 67, 54, 43.

Infrared absorption spectrum (D-ATR): νmax=3421, 2931, 2857, 1740, 1366, 1242, 1049, 725.

Example 10: Preparation of (7Z)-10-chloro-7-decenyl Acetate (4: $X^2$=Cl; a=6)

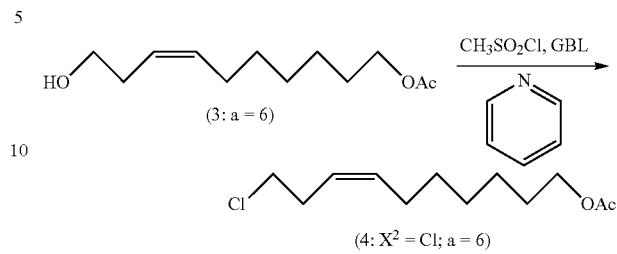

(7Z)-10-hydroxy-7-decenyl acetate (3: a=6) (17.52 g, 0.077 mol, purity 93.73%) obtained in Example 9, pyridine (13.13 g, 0.17 mol), and GBL (55.32 g) were placed in a reactor and stirred at 0 to 10° C. for 26 minutes.

Subsequently, methanesulfonyl chloride (14.79 g, 0.13 mol) was added dropwise at 0 to 10° C. After the completion of the dropwise addition, the temperature was raised to 60 to 65° C., and the reaction mixture was stirred for 7 hours. After the completion of the stirring, water (92.22 g) and subsequently hexane (92.22 g) were added, followed by phase separation. The aqueous phase was removed to obtain the organic phase. The organic phase thus obtained was washed with an aqueous acetic acid solution (acetic acid (9.22 g) and water (92.22 g)), and subsequently an aqueous sodium hydrogen carbonate solution (sodium hydrogen carbonate (4.61 g) and water (92.22 g)). The organic phase thus obtained was concentrated at a reduced pressure. The residue was subjected to a column chromatography (ethyl acetate/n-hexane=5/1) to obtain (7Z)-10-chloro-7-decenyl acetate (4: $X^2$=Cl; a=6) (18.28 g, 0.077 mol, purity 97.60%) in a yield of 100.00%.

The following is the spectrum data of the (7Z)-10-chloro-7-decenyl acetate (4: $X^2$=Cl; a=6) thus prepared.

Nuclear magnetic resonance spectrum: $^1$H-NMR (500 MHz, CDCl$_3$): δ=1.27-1.40 (6H, m), 1.61 (2H, quin-like, J=6.9 Hz), 2.01-2.06 (2H, m), 2.03 (3H, s), 2.50 (2H, q-like, J=7.1 Hz), 3.49 (2H, t, J=6.9 Hz), 4.04 (2H, t, J=6.9 Hz), 5.36 (1H, dtt, J=10.7 Hz, 7.3 Hz, 1.5 Hz), 5.51 (1H, ddt, J=10.7 Hz, 7.3 Hz, 1.5 Hz); $^{13}$C-NMR (500 MHz, CDCl$_3$): δ=20.96, 25.75, 27.23, 28.51, 28.79, 29.32, 30.65, 44.17, 64.50, 124.99, 132.97, 171.16.

Mass spectrum: EI-mass spectrum (70 eV): m/z 172 ($M^+$–60), 136, 116, 95, 81, 67, 43.

Infrared absorption spectrum (D-ATR): νmax=2932, 2857,1739, 1366, 1240, 1038, 734.

Example 11: Preparation of (7Z)-7,9-decadien-1-yl acetate (5: a=6)

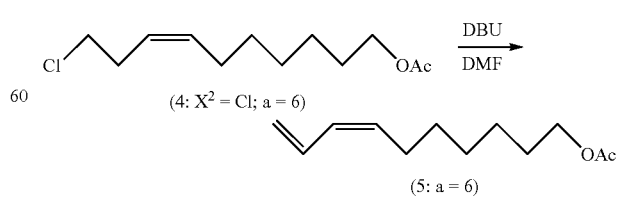

The (7Z)-10-chloro-7-decenyl acetate (4: $X^2$=Cl; a=6) (4.84 g, 0.020 mol, purity 97.60%) thus obtained in Example 10, and DMF (30.00 g) were placed in a reactor and stirred at 15 to 25° C. for 5 minutes.

Subsequently, DBU (9.27 g, 0.061 mol) was added dropwise at 15 to 25° C. After the completion of the dropwise addition, the temperature was raised to 75 to 85° C., and the reaction mixture was stirred for 6.5 hours. After the completion of the stirring, water (100.00 g) and subsequently hexane (50.00 g) were added, followed by phase separation. The aqueous phase was removed to obtain the organic phase. The organic phase thus obtained was concentrated at a reduced pressure. The residue was subjected to a column chromatography (ethyl acetate/n-hexane=80/1) to obtain (7Z)-7,9-decadien-1-yl acetate (5: a=6) (3.26 g, 0.016 mol, purity 97.54%) in a yield of 79.82%.

The following is the spectrum data of the (7Z)-7,9-decadien-1-yl acetate (5: a=6) thus prepared.

Nuclear magnetic resonance spectrum: $^1$H-NMR (500 MHz, CDCl$_3$): δ=1.28-1.44 (6H, m), 1.61 (2H, quin-like, J=6.9 Hz), 2.03 (3H, s), 2.18 (2H, dt, J=7.3 Hz, 7.3 Hz), 4.04 (2H, t, J =6.9 Hz), 5.07 (1H, d, J=9.9 Hz), 5.17 (1H, dd, J=17. 0 Hz, 1.9 Hz), 5.43 (1H, q-like, J=8.1 Hz), 5.99 (1H, dd, J=11.1 Hz, 11.1 Hz), 6.62 (1H, ddd, J=16.9 Hz, 10.5 Hz, 1.2 Hz); $^{13}$C-NMR (500 MHz, CDCl$_3$): δ=20.95, 25.73, 27.53, 28.51, 28.74, 29.38, 64.51, 116.78, 129.26, 132.20, 132.65, 171.14.

Mass spectrum: EI-mass spectrum (70 eV): m/z 196 (M$^+$), 136, 121, 107, 93, 79, 67, 54, 43.

Infrared absorption spectrum (D-ATR): νmax=2932, 2857,1741, 1366, 1240, 1036, 903, 607.

Example 12: Preparation of (7Z)-7,9-decadien-1-ol (6: a=6)

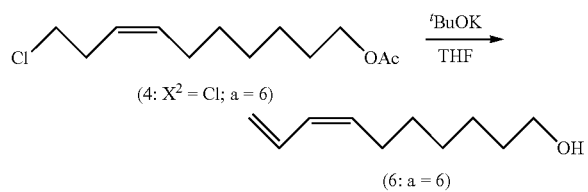

Potassium tert-butoxide (13.66 g, 0.12 mol) and tetrahydrofuran (30.44 g) were placed in a reactor and stirred at −5 to 5° C. for 26 minutes.

Subsequently, (7Z)-10-chloro-7-decenyl acetate (4: X$^2$=Cl; a=6) (4.84 g, 0.020 mol, purity 97.60%) obtained in Example 10 was added dropwise at 0 to 10° C. After the completion of the dropwise addition, the temperature was raised to 20 to 25° C., and the reaction mixture was stirred for 5.5 hours. After the completion of the stirring, water (100.00 g) and subsequently hexane (70.00 g) were added, followed by phase separation. The aqueous phase was removed to obtain the organic phase. The organic phase thus obtained was concentrated at a reduced pressure. The residue was subjected to a column chromatography (ethyl acetate/n-hexane=20/1) to obtain (7Z)-7,9-decadien-1-ol (6: a=6) (2.27 g, 0.013 mol, purity 87.37%) in a yield of 63.34%.

The following is the spectrum data of the (7Z)-7,9-decadien-1-ol (6: a=6) thus prepared.

Nuclear magnetic resonance spectrum: $^1$H-NMR (500 MHz, CDCl$_3$): δ=1.29-1.43 (6H, m), 1.55 (2H, quin-like, J=6.9 Hz), 1.66 (1H, br.s), 2.18 (2H, q-like, J=7.2 Hz), 3.62 (2H, t, J=6.5 Hz), 5.07 (1H, d, J=10.0 Hz), 5.17 (1H, dd, J=16.8 Hz, 1.9 Hz), 5.44 (1H, q-like, J=8.1 Hz), 5.99 (1H, dd, J=11.1 Hz, 11.1 Hz), 6.62 (1H, dddd, J=16.8 Hz, 10.5 Hz, 10.5 Hz, 1.2 Hz); $^{13}$C-NMR (500 MHz, CDCl$_3$): δ=25.53, 27.56, 28.91, 29.47, 32.63, 62.86, 116.73, 129.18, 132.23, 132.77.

Mass spectrum: EI-mass spectrum (70 eV): m/z 154 (M$^+$), 136, 121, 107, 93, 79, 67, 54, 41.

Infrared absorption spectrum (D-ATR): νmax=3334, 2931, 2856, 1463, 1434, 1056, 997, 902, 785, 726, 656.

Example 13: Preparation of (7Z)-7,9-decadien-1-ol (6: a=6)

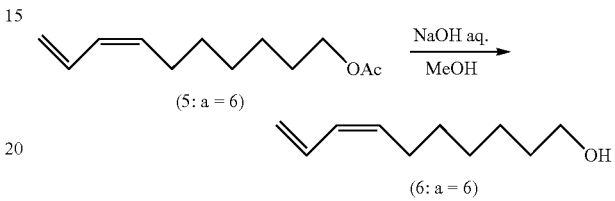

(7Z)-7,9-decadien-1-yl acetate (5: a=6) (3.00 g, 0.015 mol, purity 97.54%) obtained in Example 11 and methanol (0.45 g) were placed in a reactor and stirred at 20 to 25° C. for 5 minutes.

Subsequently, an aqueous 25% by mass sodium hydroxide solution (2.53 g, 0.016 mol as sodium hydroxide) was added dropwise at 20 to 25° C. After the completion of the dropwise addition, the temperature was raised to 60 to 65° C., and the reaction mixture was stirred for 3 hours. After the completion of the stirring, water (40.00 g) and subsequently hexane (40.00 g) were added, followed by phase separation. The aqueous phase was removed to obtain the organic phase. The organic phase thus obtained was concentrated at a reduced pressure. The residue was subjected to a column chromatography (ethyl acetate/n-hexane=20/1) to obtain (7Z)-7,9-decadien-1-ol (6: a=6) (2.31 g, 0.015 mol, purity 99.55%) in a yield of 100.00%.

The various spectrum data of the (7Z)-7,9-decadien-1-ol (6: a=6) thus prepared were same as those obtained in Example 11.

Example 14: Preparation of (3Z)-14-chloro-3-tetradecen-1-ol (2: X$^1$=Cl; a=10)

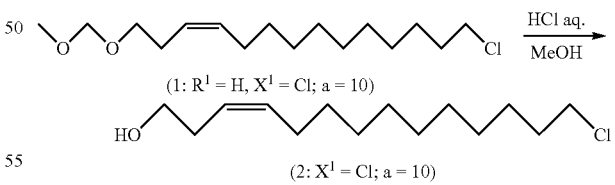

(3Z)-14-Chloro-3-tetradecenyl methoxymethyl ether (1: R$^1$=H, X$^1$=Cl; a=10) (114.44 g, 0.36 mol, purity 92.00%) obtained in Example 4, methanol (181.00 g, 5.65 mol), and 20% by mass hydrochloric acid (18.10 g, 0.099 mol as hydrogen chloride) were placed in a reactor equipped with a distillation column, and the reaction mixture was heated to 60° C. and stirred for 3 hours. After the completion of the stirring, the internal temperature was raised to 65 to 70° C., and a mixture of dimethoxymethane and methanol by-produced was distilled off from the distillation column. The reaction mixture during the reaction was sampled, and when the reaction rate reached 100%, water (400.00 g) and subsequently hexane (300.00 g) were added, followed by phase separation. The aqueous phase was removed to obtain the organic phase. The organic phase thus obtained was concentrated at a reduced pressure, and the concentrate was subjected to distillation at a reduced pressure to obtain (3Z)-14-chloro-3-tetradecen-1-ol (2: X¹=Cl; a=10) (91.31 g, 0.36 mol, purity 97.58%, b.p.=152.1 to 154.0° C./0.40 kPa (3.0 mmHg)) in a yield of 99.73%.

The following is the spectrum data of the (3Z)-14-chloro-3-tetradecen-1-ol (2: X¹=Cl; a=10) thus prepared.

Nuclear magnetic resonance spectrum: $^1$H-NMR (500 MHz, CDCl$_3$): δ=1.23-1.37 (12H, m), 1.37-1.45 (2H, m), 1.55 (1H, br.s), 1.76 (2H, quin-like, J=7.3 Hz), 2.05 (2H, q-like, J=7.1 Hz), 2.32 (2H, q-like, J=6.9 Hz), 3.52 (2H, t, J=6.9 Hz), 3.63 (2H, t, J=6.5 Hz), 5.35 (1H, dtt, J=10.7 Hz, 7.3 Hz, 1.5 Hz), 5.55 (1H, dtt, J=10.'7 Hz, 7.3 Hz, 1.5 Hz); $^{13}$C-NMR (500 MHz, CDCl$_3$): δ=26.84, 27.32, 28.83, 29.23, 29.39, 29.42, 29.44, 29.64, 30.76, 32.61, 45.14, 62.29, 124.93, 133.45.

Mass spectrum: EI-mass spectrum (70 eV): m/z 245 (M$^+$-1), 228, 200, 186, 172, 158, 144, 109, 95, 82, 68, 55, 41.

Infrared absorption spectrum (D-ATR): νmax=3,330, 2,925, 2854, 1465, 1048, 723.

Example 15: Preparation of (11Z)-14-hydroxy-11-tetradecenyl Acetate (3: a=10)

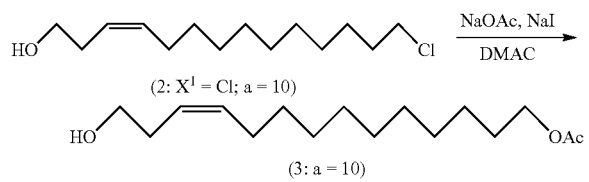

(3Z)-14-Chloro-3-tetradecen-1-ol (2: X¹=Cl; a=10) (70.45 g, 0.28 mol, purity 97.58%) obtained in Example 14, sodium acetate (40.37 g, 0.49 mol), sodium iodide (2.77 g, 0.018 mol), and DMAC (34.92 g) were placed in a reactor at room temperature and stirred at 125 to 135° C. for 5.5 hours. After the completion of the stirring, the reaction mixture was cooled to 50 to 60° C., and water (171.30 g) was added, followed by phase separation. The aqueous phase was removed to obtain the organic phase. The organic phase thus obtained was-concentrated at a reduced pressure, and the concentrate was subjected to distillation at a reduced pressure to obtain (11Z)-14-hydroxy-11-tetradecenyl acetate (3: a=10) (66.20 g, 0.23 mol, purity 93.95%) in a yield of 82.68%.

The following is the spectrum data of the (11Z)-14-hydroxy-11-tetradecenyl acetate (3: a=10) thus prepared.

Nuclear magnetic resonance spectrum: $^1$H-NMR (500 MHz, CDCl$_3$): δ=1.22-1.37 (14H, m), 1.60 (2H, quin-like, J=6.9 Hz), 1.65 (1H, br.s), 2.03 (3H, s), 2.04 (2H, q-like, J=7.3 Hz), 2.31 (2H, dt, J=6.9 Hz, 6.9 Hz), 3.62 (2H, t, J=6.5 Hz) , 4.03 (2H, t, J=6.9 Hz), 5.34 (1H, dtt, J=10.7 Hz, 7.3 Hz, 1.5 Hz), 5.53 (1H, dtt, J=10.7 Hz, 7.3 Hz, 1.6 Hz); $^{13}$C-NMR (500 MHz, CDCl$_3$): δ=20.95, 25.83, 27.30, 28.54, 29.17, 29.20, 29.41, 29.43, 29.62,30.75, 62.26, 64.62, 124. 95, 133.34, 171.24.

Mass spectrum: EI-mass spectrum (70 eV): m/z 252 (M$^+$-18), 180, 166, 152, 138, 124, 110, 96, 82, 67, 43.

Infrared absorption spectrum (D-ATR): νmax=3434, 2926, 2854, 1741, 1466, 1366, 1240, 1047, 722.

Example 16: Preparation of (11Z)-14-chloro-11-tetradecenyl Acetate (4: X²=Cl; a=10)

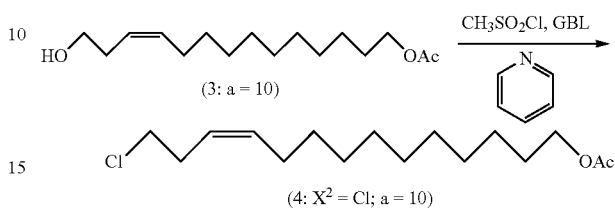

(11Z)-14-Hydroxy-11-tetradecenyl acetate (3: a=10) (16.46 g, 0.057 mol, purity 93.95%), pyridine (8.55 g, 0.11 mol) obtained in Example 15 and GBL (36.02 g) were placed in a reactor and stirred at 0 to 10° C. for 13 minutes.

Subsequently, methanesulfonyl chloride (9.63 g, 0.084 mol) was added dropwise at 0 to 10° C. After the completion of the dropwise addition, the temperature was raised to 60 to 65° C., and the reaction mixture was stirred for 7 hours. After the completion of the stirring, water (60.04 g) and subsequently hexane (60.04 g) were added, followed by phase separation. The aqueous phase was removed to obtain the organic phase. The organic phase thus obtained was washed with an aqueous acetic acid solution (acetic acid (6.00 g) and water (60.04 g)), and subsequently an aqueous sodium hydrogen carbonate solution (sodium hydrogen carbonate (3.00 g) and water (60.04 g)). The organic phase thus obtained was concentrated at a reduced pressure. The residue was subjected to a column chromatography (ethyl acetate/n-hexane=5/1) to obtain (11Z)-14-chloro-11-tetradecenyl acetate (4: X²=Cl; a=10) (15.51 g, 0.052 mol, purity 97.69%) in a yield of 91.71%.

The following is the spectrum data of the (11Z)-14-chloro-11-tetradecenyl acetate (4: X²=Cl; a=10) thus prepared.

Nuclear magnetic resonance spectrum: $^1$H-NMR (500 MHz, CDCl$_3$): δ=1.23-1.38 (14H, m), 1.60 (2H, quin-like, J=6.9 Hz), 2.03 (3H, s), 2.03 (2H, q-like, J=7.0 Hz), 2.50 (2H, dt, J=6.9 Hz, 6.9 Hz), 3.49 (2H, t, J=6.9 Hz), 4.04 (2H, t, J=6.9 Hz), 5.36 (1H, dtt, J=10.7 Hz, 7.3 Hz, 1.5 Hz), 5.52 (1H, dtt, J=10.7 Hz, 7.3 Hz, 1.5 Hz); $^{13}$C-NMR (500 MHz, CDCl$_3$): δ=20.97, 25.86, 27.34, 28.56, 29.19, 29.42, 29.45, 29.47, 30.67, 44.20, 64.61, 124.78, 133. 24, 171.18.

Mass spectrum: EI-mass spectrum (70 eV): m/z 228 (M$^+$-60), 192, 177, 163, 149, 135, 116, 95, 81, 67, 43.

Infrared absorption spectrum (D-ATR): νmax=2926, 2854, 1741, 1465, 1365, 1239, 1038, 723.

Example 17: Preparation of (11Z)-11,13-tetradecadien-1-yl Acetate (5: a=10)

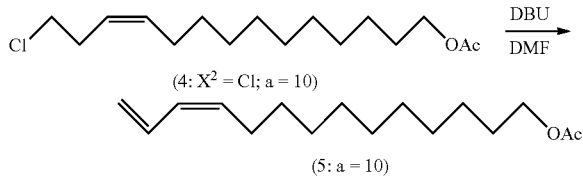

(11Z)-14-Chloro-11-tetradecenyl acetate (4: $X^2$=Cl; a=10) (5.97 g, 0.020 mol, purity 97.69%) obtained in Example 16 and DMF (30.00 g) were placed in a reactor and stirred at 15 to 25° C. for 5 minutes.

Subsequently, DBU (9.23 g, 0.061 mol) was added dropwise at 15 to 25° C. After the completion of the dropwise addition, the temperature was raised to 75 to 85° C., and the reaction mixture was stirred for 5 hours. After the completion of the stirring, water (100.00 g) and subsequently hexane (50.00 g) were added, followed by phase separation. The aqueous phase was removed to obtain the organic phase. The organic phase thus obtained was concentrated at a reduced pressure. The residue was subjected to a column chromatography (ethyl acetate/n-hexane=80/1) to obtain (11Z)-11,13-tetradecadien-1-yl acetate (5: a=10) (4.37 g, 0.017 mol, purity 98.82%) in a yield of 84.43%.

The following is the spectrum data of the (11Z)-11,13-tetradecadien-1-yl acetate (5: a=10) thus prepared.

Nuclear magnetic resonance spectrum: $^1$H-NMR (500 MHz, CDCl$_3$): δ=1.24-1.41 (14H, m), 1.61 (2H, quin-like, J=6.9 Hz), 2.04 (3H, s), 2.17 (2H, ddt, J=1.5 Hz, 7.4 Hz, 7.4 Hz), 4.04 (2H, t, J=6.9 Hz), 5.07 (1H, d, J=10.4 Hz), 5.17 (1H, dd, J=16.8 Hz, 1.9 Hz), 5.44 (1H, q-like, J=8.8 Hz), 5.99 (1H, t, J=11.1 Hz), 6.63 (1H, dddd, J=16.8 Hz, 10.5 Hz, 10.5 Hz, 1.2 Hz); $^{13}$C-NMR (500 MHz, CDCl$_3$): δ=20.98, 25.87, 27.69, 28.57, 29.15, 29.17, 29.20, 29.41, 29.45, 29.57, 64.62, 116.63, 129.10, 132.31, 133.00, 171.17.

Mass spectrum: EI-mass spectrum (70 eV): m/z 252 (M$^+$), 192, 163, 149, 135, 121, 107, 95, 81, 67, 55, 43.

Infrared absorption spectrum (D-ATR): νmax=2926, 2855, 1742, 1365, 1238, 1039, 902, 607.

The invention claimed is:

1. A process for preparing a terminal conjugated alkadien-1-yl acetate compound of the following general formula (5):

$$CH_2=CHCH=CH(CH_2)_a OAc \qquad (5)$$

wherein "a" represents an integer of 3 to 14, and Ac represents an acetyl group, the process comprising:
dealkoxymethylating a haloalkenyl alkoxymethyl ether compound of the following general formula (1):

$$R^1 CH_2 OCH_2 OCH_2 CH_2 CH=CH(CH_2)_a X^1 \qquad (1)$$

wherein $R^1$ represents a hydrogen atom, an n-alkyl group having 1 to 9 carbon atoms, or a phenyl group, $X^1$ represents a halogen atom, and "a" is as defined above to prepare a halo-3-alken-1-ol compound of the following general formula (2):

$$HOCH_2 CH_2 CH=CH(CH_2)_a X^1 \qquad (2)$$

wherein $X^1$ and "a" are as defined above;
acetoxylating the halo-3-alken-1-ol compound (2) to prepare a hydroxyalkenyl acetate compound of the following general formula (3):

$$HOCH_2 CH_2 CH=CH(CH_2)_a OAc \qquad (3)$$

wherein "a" and Ac are as defined above;
halogenating the hydroxyalkenyl acetate compound (3) to prepare a haloalkenyl acetate compound of the following general formula (4):

$$X^2 CH_2 CH_2 CH=CH(CH_2)_a OAc \qquad (4)$$

wherein $X^2$ represents a halogen atom, and "a" and Ac are as defined above; and
subjecting the haloalkenyl acetate compound (4) to an elimination reaction in the presence of a base to prepare the terminal conjugated alkadien-1-yl acetate compound (5).

2. A process for preparing a terminal conjugated alkadien-1-ol compound of the following general formula (6):

$$CH_2=CHCH=CH(CH_2)_a OH \qquad (6)$$

wherein "a" is as defined above,
the process comprising:
the process according to claim 1 for preparing the terminal conjugated alkadien-1-yl acetate compound (5), and
deacetylating the terminal conjugated alkadien-1-yl acetate compound (5) to prepare the terminal conjugated alkadien-1-ol compound (6).

3. The process for preparing the terminal conjugated alkadien-1-ol compound (6) according to claim 2, wherein the elimination reaction and the deacetylation are carried out in parallel in the presence of a base.

4. A haloalkenyl alkoxymethyl ether compound of the following general formula (1):

$$R^1 CH_2 OCH_2 OCH_2 CH_2 CH=CH(CH_2)_a X^1 \qquad (1)$$

wherein $R^1$ represents a hydrogen atom, an n-alkyl group having 1 to 9 carbon atoms, or a phenyl group, $X^1$ represents a halogen atom, and "a" represents an integer of 3 to 14.

5. The haloalkenyl alkoxymethyl ether compound of the following general formula (1) according to claim 4, wherein "a" represents an integer of 6 to 10.

6. The haloalkenyl alkoxymethyl ether compound of the following general formula (1) according to claim 5, wherein "a" represents an integer of 6, 7 or 10.

* * * * *

UNITED STATES PATENT AND TRADEMARK OFFICE
CERTIFICATE OF CORRECTION

| | | |
|---|---|---|
| PATENT NO. | : 11,560,349 B2 | Page 1 of 1 |
| APPLICATION NO. | : 17/489905 | |
| DATED | : January 24, 2023 | |
| INVENTOR(S) | : Miyake et al. | |

It is certified that error appears in the above-identified patent and that said Letters Patent is hereby corrected as shown below:

In the Specification

Column 3, Line 58, Formula 1: Please correct "R'CH$_2$OCH$_2$OCH$_2$CH$_2$CH=CH(CH$_2$)$_a$X$^1$" to read --R$^1$CH$_2$OCH$_2$OCH$_2$CH$_2$CH=CH(CH$_2$)$_a$X$^1$--

Column 20, Line 31: Please correct "le in general" to read --R$^1$ in general--

Column 25, Lines 44-45: Please remove the paragraph break between '(4:' and 'a=6).'

Column 28, Line 23: Please correct "(127,)" to read --(12Z)--

Column 30, Line 32: Please insert a paragraph break between 'acetate;' and 'and 15,17-'

Column 40, Line 39: Please correct "(M$^+$-1)" to read --(M$^+$)--

Column 41, Line 56: Please correct "δ32 1.25" to read --δ=1.25--

Column 45, Line 18: Please correct "J=10.'7 Hz" to read --J=10.7 Hz--

Signed and Sealed this
Twelfth Day of September, 2023

Katherine Kelly Vidal
*Director of the United States Patent and Trademark Office*